United States Patent [19]
Vogelstein et al.

[11] Patent Number: 5,527,676
[45] Date of Patent: Jun. 18, 1996

[54] DETECTION OF LOSS OF THE WILD-TYPE P53 GENE AND KITS THEREFOR

[75] Inventors: Bert Vogelstein; Suzanne J. Baker; Eric R. Fearon; Janice M. Nigro, all of Baltimore, Md.

[73] Assignee: The Johns Hopkins University, Baltimore, Md.

[21] Appl. No.: 47,041

[22] Filed: Mar. 22, 1993

Related U.S. Application Data

[63] Continuation of Ser. No. 928,661, Aug. 17, 1992, abandoned, which is a continuation of Ser. No. 446,584, Dec. 6, 1989, abandoned, which is a continuation-in-part of Ser. No. 330,566, Mar. 29, 1989, abandoned.

[51] Int. Cl.$^6$ .............................. C12Q 1/68; C07H 21/04
[52] U.S. Cl. .............. 435/6; 435/69.1; 435/810; 436/501; 436/63; 514/44; 536/23.1; 536/24.1; 536/24.31; 536/24.32; 536/24.33; 935/77; 935/78
[58] Field of Search .................................. 435/5, 6, 69.1, 435/810; 514/44; 436/501, 63; 536/22.1, 23.1, 24.1, 24.31-33; 935/77, 78, 88

[56] References Cited

U.S. PATENT DOCUMENTS 4,683,202  7/1987  Mullis ........................................ 435/91

OTHER PUBLICATIONS

Lamb et al. (1986), Mol. Cell. Biol., vol. 6, No. 5, pp. 1379–1385.
Zakut–Houri et al. (1985), EMBO J., vol. 4, No. 5, pp. 1251–1255.
Harris et al. (1986) Mol. Cell. Biol., vol. 6, No. 12, pp. 4650–4656.
Matlashewski et al. (1987) Mol. Cell. Biol., vol. 7, No. 2, pp. 961–963.
Buchman et al. (1988), Gene, vol. 70, pp. 245–252.
Green, "When the Products of Oncogenes and Anti–Oncogenes Meet," Cell (1989), 56:1–3.
DeCaprio et al., "SV40 Large Tumor Antigen Forms a Specific Complex with the Product of the Retinobastoma Susceptibility Gene," Cell (1988), 54:275–283.
Hinds et al., "Mutation is Required to Activate the p53 GEne for Cooperation with the ras Oncogene and Transformation," J. Virol., (1989), 63:739–746.
Finlay et al., "Activating Mutations for Transformation by p53 Produce a Gene Product that Forms an hsc70–p53 Complex with an Altered Half–Life," Molecular and Cellular Biology (1988), 8:531–539.
Mercer et al., "Microinjection of Monoclonal Antibody to Protein p53 Inhibits Serum–Induced DNA Synthesis in 3T3 Cells," Proc. Natl. Acad. Sci. USA (1982), 79:6309–6312.
Hicks et al., "Integration of Friend Murine Leukemia Virus into Both Alleles of the p53 Oncogene in an Erythroleukemic Cell Line," J. Virol. (1988), 62:4752–4755.
Milner et al., "SV40–53K Antigen: A Possible Role for 53K in Normal Cells," Virology (1981), 112:785–788.
Sturzbecher et al., "Characterization of Mutant p53–hsp72/73 Protein–Protein Complexes by Transient Expression in Monkey COS Cells," Molecular and Cellular Biology (1988), 8:3740–3747.
Eliyahu et al., "Meth A Fibrosarcoma Cells Express Two Transforming Mutant p53 Species," Oncogene (1988), 3:313–321.
Rovinski et al., "Immortalization of Rat Embryo Fibroblasts by the Cellular p53 Oncogene," Oncogene (1988), 2:445–452.

(List continued on next page.)

*Primary Examiner*—W. Gary Jones
*Assistant Examiner*—Ardin H. Marschel
*Attorney, Agent, or Firm*—Banner & Allegretti, Ltd.

[57] ABSTRACT

Methods and kits are provided for assessing mutations and/or loss of the p53 gene in human tumors. Both deletion mutations and point mutations in p53 are observed in the same human tumor cells and these mutations are clonal within the cells of the tumor. Loss of wild-type p53 genes is responsible for neoplastic progression.

57 Claims, 8 Drawing Sheets

OTHER PUBLICATIONS

Eliyahu et al., "Participation of p53 Cellular Tumour Antigen in Transformation of Normal Embryonic Cells," Nature (1984), 312:646–649.

Parada et al., "Cooperation Between Gene Encoding p53 Tumour Antigen and Ras in Cellular Transformation," Nature (1984) 312:649–651.

DeLeo et al., "Detection of a Transformation–Related Antigen in Chemically Induced Sarcomas and Other Transformed Cells of the Mouse," Proc. Natl. Acad. Sci. USA, (1979), 76:2420–2424.

Reich et al., "Growth Regulation of a Cellular Tumour Antigen, p53, in Non–transformed Cells," Nature (1984), 308:199–201.

Jenkins et al., "Cellular Immortalization by a cDNA Clone Encoding the Transformation–Associated Phosphoprotein p53," Nature (1984), 312:651–654.

Koshland, "p53 Sweeps Through Cancer Research", *Science*, 262:1958–1959 (1993).

DeCaprio, et al., "SV40 Large Tumor Antigen Forms a Specific Complex With the Product of the Retinoblastoma Susceptibility Gene", *Cell* 54:275–283 (1988).

Harlow, et al., "Association of Adenovirus Early–Region 1A Proteins With Cellular Polypeptides", *Molecular and Cellular Biology*, 6(5):1579–1589 (1986).

Harlow, et al., "Monoclonal Antibodies Specific for Simian Virus 40 Tumor Antigens", *Journal of Virology*, 39(3):861–869 (1981).

Gannon, et al., "p53 and DNA Polymerase $\alpha$ Complete for Binding to SV40 T Antigen", *Nature*, 329:456–458 (1987).

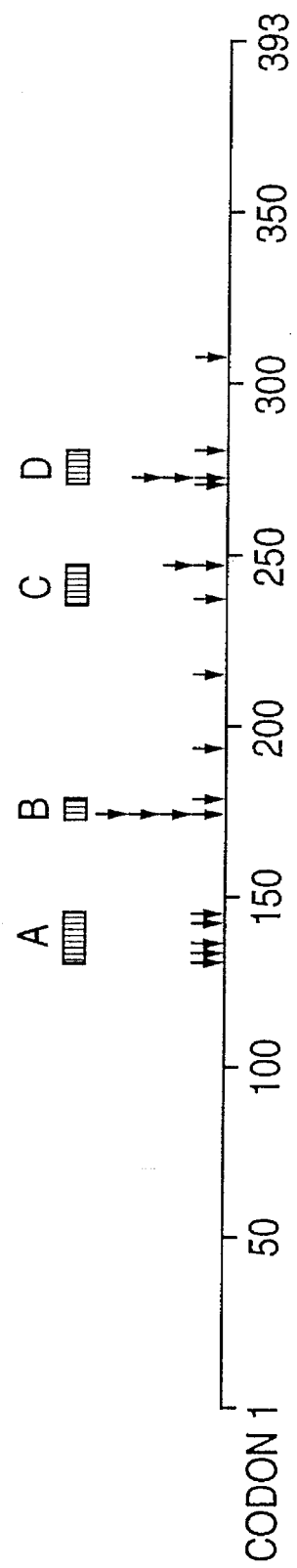

DETECTION OF LOSS OF THE WILD-TYPE P53 GENE AND KITS THEREFOR

The U.S. Government has a paid-up license in this invention and the right in limited circumstances to require the patent owner to license others on reasonable terms as provided for by the terms of grant numbers GM07309, GM07184, HD20619, CA42857, CA28854, CA47527, CA35494, NS23427 and CA43460 awarded by the National Institutes of Health.

This application is a continuation of Ser. No. 07/928,661; filed Aug. 17, 1992, now abandoned, which is a continuation, of Ser. No. 07/446,584, filed Dec. 6, 1989, now abandoned which is a continuation-in-part of Ser. No. 07/330,566, filed Mar. 29, 1989, now abandoned.

TECHNICAL AREA OF THE INVENTION

The invention relates to the area of cancer diagnostics. More particularly, the invention relates to detection of the loss and or alteration of wild-type p53 genes from tumor tissues.

BACKGROUND OF THE INVENTION

Recent studies have elucidated several genetic alterations that occur during the development of colorectal tumors, the most common of which are deletions of the short arm of chromosome 17 (17p). While some genetic alterations such as RAS gene mutations, appear to occur relatively early during colorectal tumor development, chromosome 17p deletions are often late events associated with the transition from the benign (adenomatous) to the malignant (carcinomatous) state. See Vogelstein et al., New England Journal of Medicine, Vol. 319, p525, 1988.

Because carcinomas are often lethal, while the precursor adenomas are uniformly curable, the delineation of the molecular events mediating this transition are of considerable importance. The occurrence of allelic deletions of chromosome 17p in a wide variety of cancers besides those of the colon, including those of the breast and lung, further emphasizes the importance of genes residing on chromosome 17p in the neoplastic process. Because allelic deletions have been reported to encompass a large area of chromosome 17p, there is a need in the art for defining the particular genetic region which is responsible for the neoplastic progression.

SUMMARY OF THE INVENTION

It is an object of the present invention to provide a method for diagnosing a neoplastic tissue of a human.

It is another object of the invention to provide a method of supplying wild-type p53 gene function to a cell which has lost said gene function.

It is yet another object of the invention to provide a kit for determination of the nucleotide sequence of the p53 gene by using the polymerase chain reaction.

It still another object of the invention to provide a nucleic acid probe for detection of mutations in the human p53 gene.

These and other objects of the invention are provided by one or more of the embodiments which are described below. In one embodiment of the present invention a method of diagnosing a neoplastic tissue of a human is provided comprising: isolating from a human a tissue suspected of being neoplastic; and detecting loss of wild-type p53 genes or their expression products from said tissue, said loss indicating neoplasia of the tissue.

In another embodiment of the present invention a method is provided for supplying wild-type p53 gene function to a cell which has lost said gene function by virtue of a mutation in the p53 gene, comprising: introducing a wild-type p53 gene into a cell which has lost said gene function such that said wild-type gene is expressed in the cell.

In yet another embodiment a kit is provided for determination of the nucleotide sequence of the p53 gene by polymerase chain reaction. The kit comprises: a set of pairs of single stranded DNA primers, said set allowing synthesis of all nucleotides of the p53 gene coding sequences.

In still another embodiment of the invention a nucleic acid probe is provided which is complementary to human wild-type p53 gene sequences and which can form mismatches with mutant p53 genes, thereby allowing their detection by enzymatic or chemical cleavage or by shifts in electrophoretic mobility.

The present invention provides the art with the information that the p53 gene is, in fact, the target of both deletional and point mutational alterations on chromosome 17p which are associated with the process of tumorigenesis. This information allows highly specific assays to be done to assess the neoplastic status of a particular tumor tissue.

BRIEF DESCRIPTION OF THE DRAWINGS

FIG. 8 maps the p53 point mutations involved in human cancer. Each of the missense mutations listed in Table 1 is indicated with an arrow. In addition, the two point mutations described previously (Baker, et al., Science, vol. 244, p. 217, 1989) in human cancers (at codons 143 and 175) are also included. The four regions containing most (86%) of the mutations are indicated by the black bars marked A–D.

DETAILED DESCRIPTION

Figure 1:
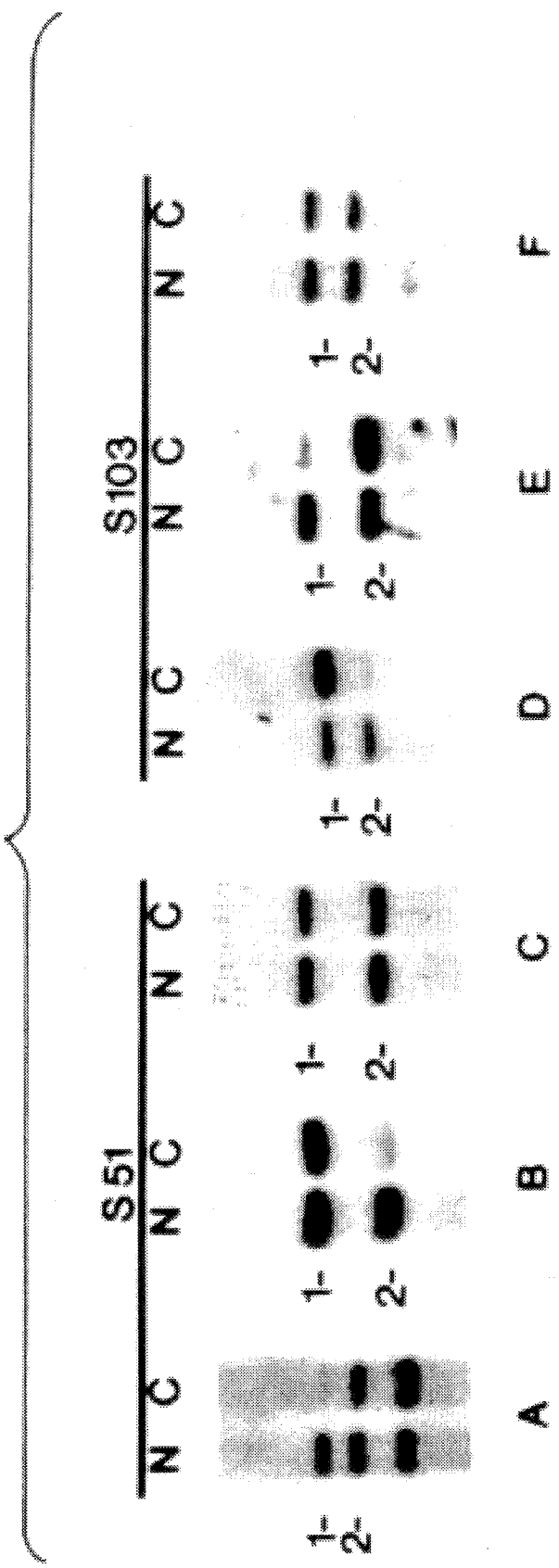
FIG. 1 demonstrates the analysis of allelic losses on chromosome 17p in the human tissue of two patients, S51 and S103.

It is a discovery of the present invention that mutational events associated with tumorigenesis occur in the p53 gene on chromosome 17p. Although it was previously known that deletion of alleles on chromosome 17p were common in certain types of cancers, it was not known that the deletions shared a common region which includes the p53 gene. Further it was not known that a second mutational event on the sister chromosome of that carrying the deletions was also affected by mutation in the p53 gene. The mutation of the sister chromosome does not involve gross rearrangements such as deletions, insertions or inversions, but rather point mutations located in a variety of positions throughout the p53 gene. Although the inventors do not wish to be bound by the following theory, it is proposed as a possible mechanism which explains the observed results. It is believed that the point mutation occurs first and the deletion event occurs second, as the latter event is correlated with the change of a tumor from an adenomatous to a carcinomatous state.

According to the diagnostic method of the present invention, loss of the wild-type p53 gene is detected. The loss may be due to either deletional and/or point mutational events. If only a single p53 allele is mutated, an early neoplastic state is indicated. However, if both alleles are mutated then a late neoplastic state is indicated. The p53 allele which is not deleted (i.e., that on the sister chromosome to the chromosome carrying the deletion) can be screened for point mutations, such as missense, and frameshift mutations. Both of these types of mutations would lead to non-functional p53 gene products. In addition, point mutational events may occur in regulatory regions, such as in the promoter of the p53 gene, leading to loss or diminution of expression of the p53 mRNA.

In order to detect the loss of the p53 wild-type gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the p53 allele (or alleles) present in the tumor tissue and sequencing that allele(s) using techniques well known in the art. Alternatively, the polymerase chain reaction can be used to amplify p53 gene sequences directly from a genomic DNA preparation from the tumor tissue. The DNA sequence of the amplified sequences can then be determined. The polymerase chain reaction itself is well known in the art. See e.g., Saiki et al., Science, Vol. 239, p. 487, 1988; U.S. Pat. Nos. 4,683,202; and 4,683,195. Specific primers which can be used in order to amplify the p53 gene will be discussed in more detail below.

Specific deletions of p53 genes can also be detected. For example, restriction fragment length polymorphism (RFLP) probes for the p53 gene or surrounding marker genes can be used to score loss of a p53 allele. Other techniques for detecting deletions, as are known in the art can be used.

Loss of wild-type p53 genes may also be detected on the basis of the loss of a wild-type expression product of the p53 gene. Such expression products include both the mRNA as well as the p53 protein product itself. Point mutations may be detected by sequencing the mRNA directly or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Alternatively, mismatch detection can be used to detect point mutations in the p53 gene or its mRNA product. While these techniques are less sensitive than sequencing, they are simpler to perform on a large number of tumors. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type p53 gene. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the p53 mRNA or DNA. The riboprobe need not be the full length of the p53 mRNA or gene but can be a segment of either. If the riboprobe comprises only a segment of the p53 mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA, vol. 85, 4397, 1988; and Shenk et al., Proc. Natl. Acad. Sci. USA, vol. 72, p. 989, 1975. Alternatively, mismatches can be detected by shifts in the electrophoretic mobility of mismatched duplexes relative to matched duplexes. See, e.g., Cariello, Human Genetics, vol. 42, p. 726, 1988. With either riboprobes or DNA probes, the cellular mRNA or DNA which might contain a mutation can be amplified using PCR (see below) before hybridization.

DNA sequences of the p53 gene from the tumor tissue which have been amplified by use of polymerase chain reaction may also be screened using allele-specific probes. These probes are nucleic acid oligomers, each of which contains a region of the p53 gene sequence harboring a known mutation. For example, one oligomer may be about 30 nucleotides in length, corresponding to a portion of the p53 gene sequence. At the position coding for the 175th codon of p53 gene the oligomer encodes an alanine, rather than the wild-type codon valine. By use of a battery of such allele-specific probes, the PCR amplification products can be screened to identify the presence of a previously identified mutation in the p53 gene. Hybridization of allele-specific probes with amplified p53 sequences can be performed, for example, on a nylon filter. Hybridization to a particular probe indicates the presence of the same mutation in the tumor tissue as in the allele-specific probe.

Loss of wild-type p53 genes can also be detected by screening for loss of wild-type p53 protein function. Although all of the functions which the p53 protein undoubtedly possesses have yet to be elucidated, at least two specific functions are known. Protein p53 binds to the SV40 large T antigen as well as to the adenovirus E1B antigen. Loss of the ability of the p53 protein to bind to either or both of these antigens indicates a mutational alteration in the protein which reflects a mutational alteration of the gene itself. Alternatively, a panel of monoclonal antibodies could be used in which each of the epitopes involved in p53 functions are represented by a monoclonal antibody. Loss or perturbation of binding of a monoclonal antibody in the panel would indicate mutational alteration of the p53 protein and thus of the p53 gene itself. Any means for detecting an altered p53 protein can be used to detect loss of wild-type p53 genes.

Mutant p53 genes or gene products can also be detected in body samples, such as, serum, stool, or other body fluids, such as urine and sputum. The same techniques discussed above for detection of mutant p53 genes or gene products in tissues can be applied to other body samples. By screening such body samples, a simple early diagnosis can be achieved for many types of cancers. In addition, the progress of chemotherapy or radiotherapy can be monitored more easily by testing such body samples for mutant p53 genes or gene products.

The method of the present invention for diagnosis of neoplastic tissue is applicable across a broad range of tumors. These include lung, breast, brain, colorectal, bladder, mesenchyme, prostate, liver as well as stomach tumors. In addition the method may be used in leukemias and osteosarcomas. It thus appears that the p53 gene has a role in the development of a broad range of tumors. The methods of diagnosis of the present invention are applicable to any rumor in which p53 has a role in tumorigenesis. The diagnostic method of the present invention is useful for clinicians so that they can decide upon an appropriate course of treatment. For example, a tumor displaying loss of both p53 alleles suggests a more aggressive therapeutic regimen than a tumor displaying loss of only one p53 allele.

The kit of the present invention is useful for determination of the nucleotide sequence of the p53 gene using the polymerase chain reaction. The kit comprises a set of pairs of single stranded DNA primers which can be annealed to sequences within or surrounding the p53 gene in order to prime amplifying DNA synthesis of the p53 gene itself. The complete set allows synthesis of all of the nucleotides of the p53 gene coding sequences. The set of primers may or may not allow synthesis of both intron and exon sequences. However, it should allow synthesis of all exon sequences.

In order to facilitate subsequent cloning of amplified sequences, primers may have restriction enzyme sites appended to their 5' ends. Thus, all nucleotides of the primers are derived from p53 sequences or sequences adjacent to p53 except the few nucleotides necessary to form a restriction enzyme site. Such enzymes and sites are well known in the art. The primers themselves can be synthesized using techniques which are well known in the art. Generally, the primers can be made using synthesizing machines which are commercially available.

In a preferred embodiment, the set of primer pairs comprises five primer pairs which are listed below. Primer pair 1: 5'-GGAATTCCACGACGGTGACACG-3' and 5'-GGAATTCGGTGTAGGAGCTGCTGG-3'; pair 2: 5'-GGAATTCCCAGAATGCCAGAGGC-3'; 5'-GGAATTCATGTGCTGTGACTGCTTG-3'; pair 3: 5'-GGAATTCCACACCCCCGCCCG-3' and 5'-GGAATTCATGCCGCCCATGCAG-3'; pair 4: 5'-GGAATTCTGACTGTACCACCATCC-3' and 5'-GGAATTCTCCATCCAGTGGTTTC-3'; pair 5: 5'-GGAATTCCCAACAACACCAGCTCC-3' and 5'-GGAATTCAAAATGGCAGGGGAGGG-3'.

The nucleic acid probes provided by the present invention are useful in the RNase protection method for detecting point mutations already discussed above. They may also be used to detect mismatches with the p53 gene or mRNA using other techniques. Mismatches can be detected using other enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, vol. 83, p. 586, 1986. If a riboprobe is used to detect mismatches with mRNA, it is complementary to the mRNA of the human wild-type p53 gene. The riboprobe thus is an anti-sense probe in that it does not code for the p53 protein because it is of the opposite polarity to the sense strand. The riboprobe generally will be radioactively labeled which can be accomplished by any means known in the art. If the riboprobe is used to detect mismatches with DNA it can be of either polarity, sense or anti-sense. Similarly, DNA probes also may be used to detect mismatches. Probes may also be complementary to mutant alleles of p53 gene. These are useful to detect similar mutations in other patients on the basis of hybridization rather than mismatches. These are discussed above and referred to as allele-specific probes.

According to the present invention a method is also provided of supplying wild-type p53 function to a cell which carries mutant p53 alleles. The wild-type p53 gene or a part of the gene may be introduced into the cell in a vector such that the gene remains extrachromosomal. In such a situation the gene will be expressed by the cell from the extrachromosomal location. If the mutant p53 genes present in the cell are expressed, then the wild-type p53 gene or gene portion should be expressed to a higher level than that of the mutant gene. This is because the mutant forms of the protein are thought to oligomerize with wild-type forms of the protein. (Eliyahu et al., Oncogene, Vol. 3, p. 313, 1988.) If a gene portion is introduced and expressed in a cell carrying a mutant p53 allele, the gene portion should encode a part of the p53 protein which is required for non-neoplastic growth of the cell. More preferred is the situation where the wild-type p53 gene or a part of it is introduced into the mutant cell in such a way that it recombines with the endogenous mutant p53 gene present in the cell. Such recombination would require a double recombination event which would result in the correction of the p53 gene mutation. Vectors for introduction of genes both for recombination and for extrachromosomal maintenance are known in the art and any suitable vector may be used.

Polypeptides or other molecules which have p53 activity may be supplied to cells which carry mutant p3 alleles. The active molecules can be introduced into the cells by microinjection or by liposomes, for example. Alternatively, some such active molecules may be taken up by the cells, actively or by diffusion. Supply of such active molecules will effect an earlier neoplastic state.

Predisposition to cancers can be ascertained by testing normal tissues of humans. For example, a person who has inherited a germline p53 mutation would be prone to develop cancers. This can be determined by testing DNA from any tissue of the person's body. Most simply, blood can be drawn and DNA extracted from the cells of the blood. Loss of a wild-type p53 allele, either by point mutation or by deletion, can be detected by any of the means discussed above. DNA can also be extracted and tested from fetal tissues for this purpose.

The following are provided for exemplification purposes only and are not intended to limit the scope of the invention which has been described in broad terms above.

EXAMPLE 1

This example demonstrates that the deletions found on chromosome 17p in human colorectal carcinomas share a common region between bands 17p12 and 17p13.3.

Twenty DNA probes detecting restriction fragment length polymorphisms (RFLPs) on chromosome 17p were used to examine the patterns of allelic losses in colorectal tumors. These probes have been mapped to seven discrete regions of 17p on the basis of their hybridization to human-rodent somatic cell hybrids containing parts of chromosome 17p (P. van Tuinen, D. C. Rich, K. M. Summers, D. H. Ledbetter, Genomics 1, 374 (1987); P. van Tuinen et al., Am. J. Hum. Gen. 43, 587 (1988); P. R. Fain et al., Genomics 1, 340 (1987); unpublished data of D. H. Ledbetter and D. F. Barker).

DNA was obtained from 58 carcinoma specimens and compared to DNA from adjacent normal colonic mucosa. Allelic losses were scored if either of the two alleles present in the normal cells was absent in the DNA from the tumor cells. Allelic deletions can be difficult to detect in DNA prepared from whole tumors because most solid tumors contain a significant number of non-neoplastic stromal and inflammatory cells. For this reason, regions of tumors containing a high proportion of neoplastic cells were identified histopathologically and isolated, and DNA was prepared from cryostat sections of these regions as described previously (S. Goelz, S. R. Hamilton, B. Vogelstein, Biochem. Biophys. Res. Commun. 130, 118 (1985); E. R. Fearon, A. Feinberg, S. R. Hamilton, B. Vogelstein, Nature 318, 377 (1985). Grossly normal colonic mucosa adjacent to the tumors was obtained from each patient and used to prepare control DNA.

The two parental alleles could be distinguished in the normal mucosa of each patient with at least 5 of the 20 RFLP markers (the "informative" markers for each case). Seventy-seven percent of the tumors exhibited allelic losses of at least 3 markers. Studies of 8 tumors which retained heterozygosity for some but not all markers on chromosome 17p enabled the definition of a common region of deletion.

FIG. 1 shows a sample of the data collected from two patients. DNA from normal (N) and carcinoma (C) tissue of patients S51 and S103 was digested with restriction endonucleases and the fragments separated by electrophoresis. After transfer to nylon filters, the DNA was hybridized to radiolabeled probes. Techniques used for DNA purification restriction endonuclease digestion, electrophoresis, transfer and hybridization were performed as described (B. Vogelstein et al., N. Engl. J. of Med. 319, 525 (1988); Goelz, supra; Fearon, supra.) Taq I digestion was used for panels A, B, C, and F, BamHI for panel D and Mspl for panel E. Autoradiographs of the washed filters are shown. The alleles designated "1" and "2" refer to the larger and smaller polymorphic alleles, respectively, present in the normal DNA samples. The probes used were: A: MCT35.2; B: EW301; C: YNH37.3; D: YNZ22.1; E: MCT.35.1; F: EW505. Deletions of allele 1 can be seen in panels A and E; deletions of allele 2 in panels B and D.

Figure 2:
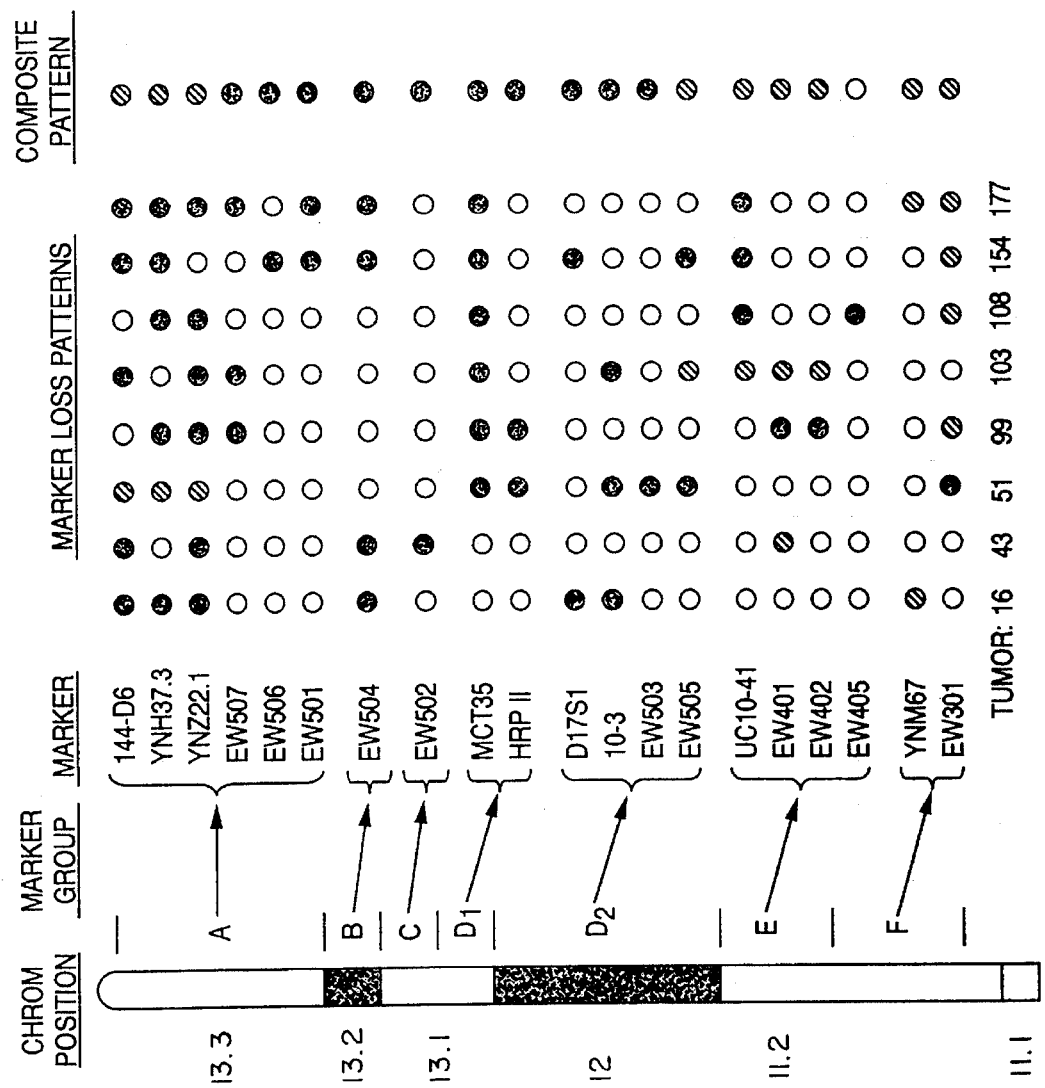
FIG. 2 shows a map of the common region of deletions on chromosome 17p in colorectal tumors. The chromosomal positions of 20 restriction fragment length polymorphism (RFLP) markers from chromosome 17p are indicated. The markers were previously mapped to seven sub-chromosomal regions (indicated A to F). Hybridization results for eight tumors are shown on the right, with patient identification numbers indicated at the bottom. A filled circle indicates loss of one parental allele in the tumor; a cross-hatched circle indicates retention of both parental alleles; an open circle indicates that the marker was not informative, i.e. the patient's normal tissue was not heterozygous for the marker. The premise of the composite pattern is that there is a single target gene on 17p. Therefore, markers for which heterozygosity was retained in any of the eight tumors (i.e., cross-hatched circles) would be outside the target locus.

The tumor from patient S51 had retained both parental alleles of three markers from the distal region of 17p, but had lost one of all more proximal markers that were formative (FIG. 1, A–C). This implied that the target of the allelic loss in this tumor was proximal to the three retained markers. Analysis of the pattern of marker loss is shown in FIG. 2. The tumor from patient S103 had retained both parental alleles at all informative loci proximal to EW505, but had allelic deletions of several more distal markers (FIG. 1, D–F). The combined data depicted in FIG. 2 indicated that the smallest common region of deletion extended between markers within band 17p12 to those within band 17p13.3. This localization is based on the assumption that the same 17p locus was the target of deletion in all of the tumors.

EXAMPLE 2

This example demonstrates that the non-deleted p53 alleles in colorectal carcinomas carrying a p53 deletion are not rearranged.

First, p53 cDNA probes detecting exons spread over 20,000 base pairs (including all protein encoding exons) [P. Lamb, L. V. Crawford, Mol. Cell. Biol. 6, 1379 (1986); R. Zakut-Houri, B. Bienz-Tadmor, D. Givol, M. Oren, EMBO J. 4, 1251 (1985); N. Harris E. Brill, O. Shahat, M. Prokocimer, T. E. Admas, Mol. Cell. Biol., 6, 4650 (1986); G. Matlashewski et al., Molec. Cell. Biol. 7, 961 (1987); V. L. Buchman et al., Gene 70, 245 (1988)] were used to examine the DNA of 82 colorectal carcinomas (50 primary specimens and 32 cell lines) in Southern blotting experiments.

No rearrangements of the p53 gene were observed with EcoR I or BamH I digests, nor were deletions of both alleles seen. Because p53 expression might be affected by gross genetic alterations further removed from p53 coding sequences, pulsed-field gel electrophoresis was used to examine large restriction fragments encompassing the p53 gene. The restriction endonucleases EcoR V, PaeR7 I, Not I, and Sal I generated p53 gene-containing fragments of 45–350kb from the DNA of normal cells. No alterations were detected in the DNA from any of 21 colorectal tumor cell lines examined with each of these four enzymes.

EXAMPLE 3

This example demonstrates that the non-deleted p53 alleles in colorectal carcinomas carrying a p53 deletion express mRNA of the normal size and in most cases normal amounts.

Northern blot experiments were performed on RNA from 22 colorectal tumors (6 primary rumors and 16 cell lines). Because p53 expression has been correlated with cellular growth and/or transformation other genes whose expression is similarly regulated were used as controls (c-myc, histone H3, and phosphoglycerate kinase).

RNA was purified from grossly normal colonic mucosa, primary carcinoma specimens or tumor cell lines, and separated by electrophoresis. Cell lines were generously provided by D. and M. Brattain or obtained from the American Type Culture Collection, Rockville, Md. Total cellular RNA was isolated by the acid-guanidinium extraction method (P. Chomczynski, N. Sacchi, Anal. Biochem. 162, 156 (1987)). Five micrograms were separated by electrophoresis through a 1.5% 2(N-morpholino) ethane sulfonic acid-formaldehyde agarose gel and electrophoretically transferred to nylon filters. The RNA was transferred to nylon filters and hybridized with a radiolabeled p53 gene probe. Labelling of the probes, hybridization, washing and autoradiography were performed as described. (Fearon et al., Science, Vol. 238, p. 193, 1987; Vogelstein et al., N. Engl. J. of Med., Vol. 319, p. 525, 1988; and Goelz, supra; and Fearon, Nature, supra). Autoradiographs were exposed for 18–24 hours.

Figure 3:
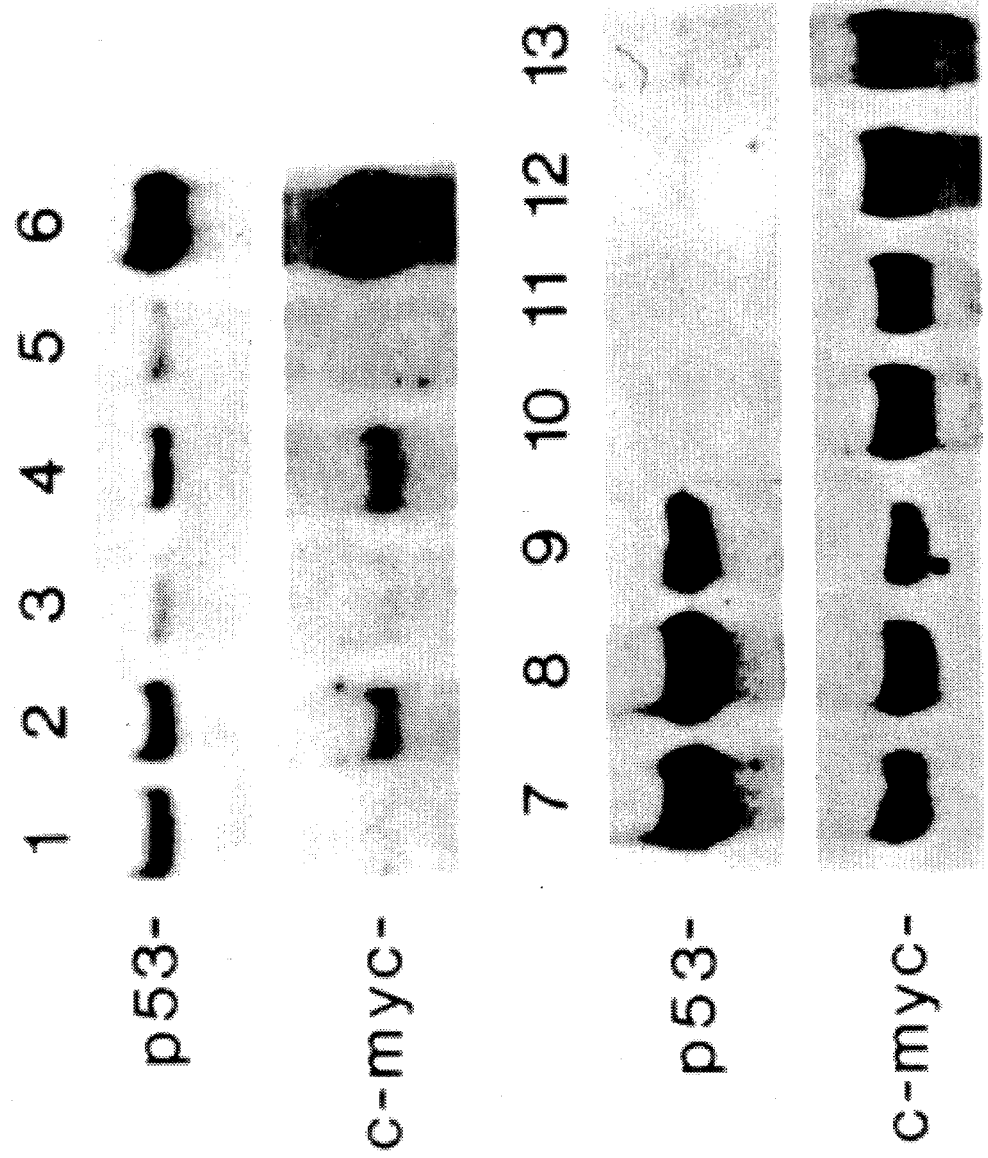
FIG. 3 shows a Northern blot analysis of p53 mRNA in colorectal tumors. The RNA in lanes 1–6 and 12 was prepared from human tissues (normal colonic mucosa or carcinoma biopsies). The RNA in lanes 7–11 and 13 was prepared from colorectal carcinoma cell lines.

The p53 probe was a 1.8 kb XbaI fragment of a p53 cDNA clone generously provided by D. Givol (EMBO J., vol. 4, p. 1251 (1985)). The c-myc probe was a 1.6 kb genomic SstI fragment containing exon 2 of c-myc (K. Alitalo et al., Proc. Nat'l. Acad. Sci. USA 80, 1707 (1983)). The signals were removed from the filter, and the blot was re-hybridized with a c-myc gene probe. Autoradiographs of the hybridized filters are shown in FIG. 3. The size of the p53 mRNA detected was 2.8 kb, and the size of the c-myc mRNA was 2.5 kb.

The RNA in lanes 1–6 and lane 12 was prepared from human tissues (normal colonic mucosa (N) or carcinoma biopsies (C)). The RNA in lanes 7–11 and 13 was prepared from colorectal carcinoma cell lines. Lanes 1, 2: Patient S345, N and C, respectively. Lanes 3, 4: Patient S353, N and C, respectively. Lanes 5, 6, Patient S369, N and C, respectively. Lane 7: SW837, Lane 8: SW480, Lane 9: LoVo, Lane 10: SW948, Lane 11: SW1417, Lane 12: Patient S115, C, Lane 13: RKO.

The size of p53 mRNA was normal (2.8 kb) in all 22 tumors. Moreover, the relative abundance of p53 gene mRNA was usually at least as great in colorectal tumor cells as in normal colonic mucosa confirming the results of Calabretta et al. (Cancer Research, Vol. 46, p. 738 (1986)). However, in four tumors, (lanes 10–13) relatively little expression of p53 mRNA was observed compared to that in the other tumors. This low level of expression of p53 was specific in that c-myc, histone H3, and phosphoglycerate kinase mRNAs were expressed in these four tumors at levels similar to those seen in other colorectal tumors and at least as high as in non-neoplastic colonic mucosa.

EXAMPLE 4

This example demonstrates that the non-deleted p53 allele in a primary tumor carries a point mutation at codon 143.

A tumor was chosen which had an allelic deletion of chromosome 17p yet expressed significant quantities of p53 mRNA. A cDNA clone originating from the remaining p53 allele was isolated and sequenced to determine whether the gene product was abnormal.

For practical reasons, a nude mouse xenograft (Cx3) of a primary tumor was selected for this test. Primary tumors contain non-neoplastic cells which could contribute p53 mRNA, while in xenografts the non-neoplastic cells (derived from the mouse) could not be the source of a human p53 cDNA clone. Cx3, like over 75% of colorectal carcinomas, had allelic deletions of several RFLP (restriction fragment length polymorphism) markers on chromosome 17 and expressed significant amounts of p53 mRNA.

A nearly full-length p53 cDNA was cloned from Cx3 mRNA using standard techniques. Double stranded cDNA was synthesized as described by U. Gubler and B. J. Hoffman, Gene 25 263 (1983) and cloned into the lambda gt10 vector. The cDNA insert was subcloned into Bluescript KS (Stratagene Cloning Systems, LaJolla, Calif.) and nested deletions were made with exonuclease III (S. Henekoff, Gene 28, 351 [1984]). Sequences were obtained from double-stranded templates using modified T7 polymerase as described by S. Tabor and C. C. Richardson, Proc. Nat'l. Acad. Sci. USA 84, 4767 (1987) and R. Kraft, J. Tardiff, K. S. Krauter and I. A. Leinwand, Biotechniques 6, 544 (1988).

The clone extended 2567 nucleotides from position -198 relative to the translation initiation site to the polyadenosine tail. The clone was sequenced by the dideoxy chain-termination method and one nucleotide difference was identified in comparison with published p53 cDNA sequences (See, Lamb, supra and SEQ ID NOS: 14–24; Zakut-Houri, supra; Harris, supra and SEQ ID NOS: 12–13; Matlashewski; supra; and Buchman, supra and SEQ ID NOS: 1–11). A transition from T to C had occurred within codon 143 (GTG to GCG), resulting in a change of the encoded amino acid from valine to alanine.

The cited references disclose wild-type p53 sequences. Some variations in the sequence are disclosed which represent polymorphisms within the human population, and not mutations. Matlachewski, supra, teaches that amino acid 72 can be either arginine (CGC), proline (CCC), or cysteine (TGC). Each of these polymorphisms were found in normal human tissues. Lamb, supra, discloses the arginine codon (CGC) at this position. Buchman, supra, and Zakut-Houri, supra, disclose the proline at codon 72. Harris, supra, discloses both arginine and proline at this position. In addition, Lamb discloses a second variant at codon 273 where histidine (CAT) is substituted for arginine (CGT). Buchman also discloses two allelic differences in the 3'-non-translated region of mRNA (nt 1949 and 2552) and in intron 6 (nt 1274). Harris also discloses a conservative amino acid difference at codon 79 which substitutes a threonine for an alanine, and a corresponding inversion of nucleotides 234 and 235.

To ensure that the sequence change was not an artifact of cDNA cloning, the polymerase chain reaction [PCR, (Saiki, et al., Science, Vol. 239, p. 487, 1988)] was used to amplify a 111 base pair (bp) sequence surrounding the presumptive mutation from genomic DNA of Cx3.

DNA was incubated in the presence of Taq polymearse with primer oligomers complementary to sequences 68 base pairs upstream and 43 base pairs downstream of codon 143. The upstream primer used was 5'-TTCCTCTTCCTGCAG-TACTCC-3'; all but 6 nucleotides of this primer were derived from the p53 intron 4 sequence determined by Buchman et al., supra. The downstream primer was 5'-GACGCGGGTGCCGGGCGG-3'. After 35 cycles of denaturation (one minute, 93°), annealing (2 minutes, 55°) and elongation (2 minutes, 70°) amplified DNA fragments of 111 bp were generated. Following electrophoresis, the 111 bp amplified fragments were eluted from a polyacrylamide gel and purified by extraction with phenol and chloroform.

Analysis of the PCR product was facilitated by the observation that the presumptive mutation created a new Hha I site (GCGC at nt 427–430). An aliquot of each of the purified DNA fragments was digested with Hha I, separated by electrophoresis on a non-denaturing polyacrylamide gel, and electrophoretically transferred to nylon filters. The fragments were hybridized with a radioactive p53 probe generated from a 1.8 kb Xba I fragment of a p53 cDNA clone provided by D. Givol (Zakot-Houri, supra).

Figure 4:
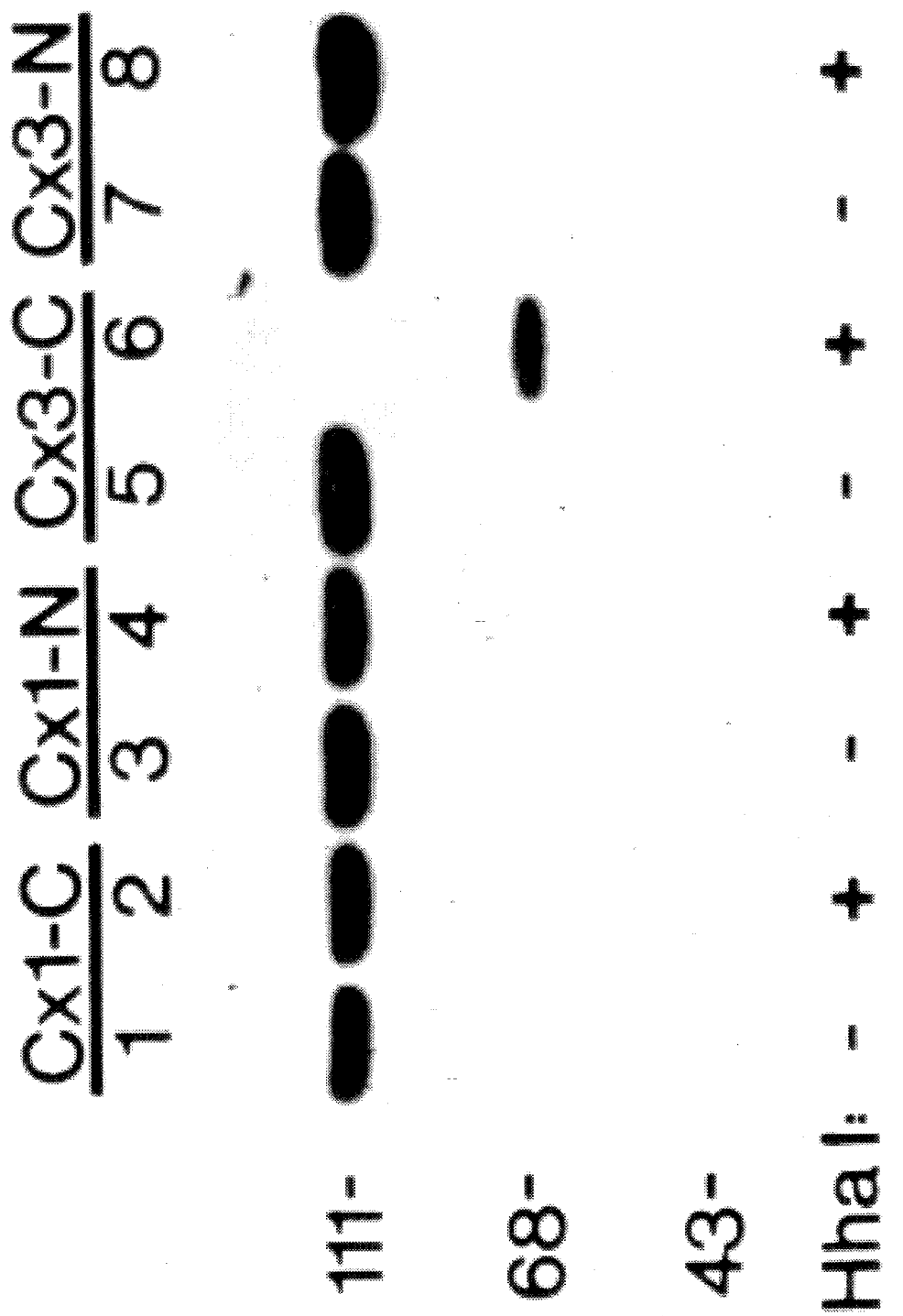
FIG. 4 shows analysis of the products of polymerase chain amplification of a 111 bp fragment surrounding the p53 gene codon 143. Lanes 1,2: colorectal tumor xenograft Cx1; lanes 3,4: normal fibroblasts from the patient providing Cx1; lanes 5,6: colorectal tumor xenograft Cx3; lanes 7,8: normal fibroblasts from the patient providing Cx3.

The 111 bp PCR product from tumor Cx3 was cleaved with Hha I to produce the expected 68 and 43 subfragments (FIG. 4, lanes 5 and 6). The 111 bp PCR product from the DNA of normal cells of the patient providing Cx3 was not cleaved with Hha I (lanes 7 and 8), nor were the PCR products of 37 other DNA samples prepared from the normal tissues, primary colorectal tumors, or xenografts of other patients (examples in FIG. 4, lanes 1–4). Therefore, the valine to alanine substitution present in this tumor was the result of a specific point mutation not present in the germline of the patient.

A small amount of a contaminating 73 base pair PCR product was present in most of the eluates; the contaminant was not cleaved by Hha I, however, so that it did not interfere with the analysis.

EXAMPLE 5

This example demonstrates that a second tumor from a different patient carried a point mutation at codon 175 of the p53 gene.

Colorectal carcinoma xenograft Cx1, like Cx3, had alleic deletions of several markers on chromosome 17p and expressed considerable amounts of normal size p53 mRNA. First strand cDNA was generated from Cx1 RNA using random hexamers in the presence of reverse transcriptase (E. Noonan and I. B. Roninson, Nucleic Acids Research 16, 10366 [1988]). This cDNA was used in five separate PCR reactions to generate fragments corresponding to nucleotides -59 to 246 (primer pair 1), 189 to 508 (primer pair 2), 443 to 740 (primer pair 3), 679 to 979 (primer pair 4), and 925 to 1248 (primer pair 5). These fragments contained all coding sequences of the p53 gene. Primer pair 1: 5'-GGAATTCCACGACGGTGACACG-3' and 5'-GGAATTCGGTGTAGGAGCTGCTGG-3'; pair 2: 5'-GGAATTCCCAGAATGCCAGAGGC-3' and 5'-GGAATTCATGTGCTGTGACTGCTTG-3'; pair 3: 5'-GGAATTCCACACCCCCGCCCG-3' and 5'-GGAATTCATGCCGCCCATGCAG-3'; pair 4: 5'-GGAATTCTGACTGTACCACCATCC-3' and 5'-GGAATTCTCCATCCAGTGGTTTC-3'; pair 5: 5'-GGAATTCCCAACAACACCAGCTCC-3' and 5'-GGAATTCAAAATGGCAGGGGAGGG-3'. All primers had extraneous nucleotides comprising EcoR I cleavage sites at their 5' ends to facilitate cloning. The PCR products were cloned in the EcoR I site of Bluescript SK and sequenced as described in Example 4. Only 1 base pair change was identified (transition from CGC to CAC) and this change at codon 175 was found in two independent clones.

Figure 5:
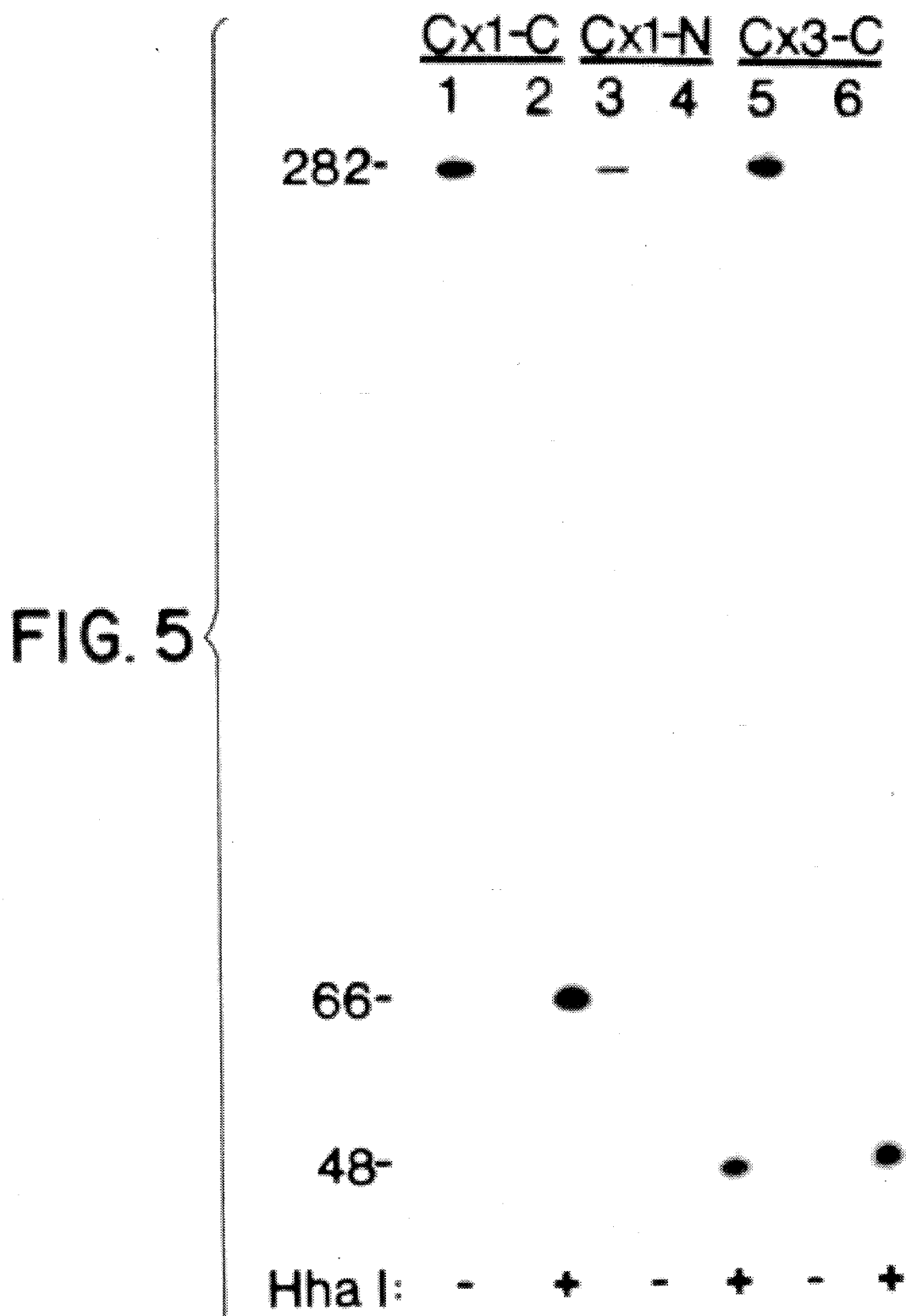
FIG. 5 shows polymerase chain reaction analysis of p53 codon 175. Lanes 1,2: colorectal tumor xenograft Cx1; lanes 3,4: normal fibroblasts from the patient providing Cx1; lanes 5,6: colorectal tumor xenograft Cx3. Samples in even numbered lanes only were digested with Hha I.

To ensure that the sequence change represented a mutation rather than a sequence polymorphism, PCR was used to amplify a fragment containing codon 175 from the genomic DNA of tumor Cx1 and normal cells. PCR was used to amplify a 319 bp fragment containing intron 5 and surrounding exon sequences. The upstream primer was the same as used for primer pair 3 and the downstream primer was 5'-CGGAATTCAGGCGGCTCATAGGGC-3'; PCR was performed as described in Example 4. Following electrophoresis through a 2% agarose gel, the 319 bp fragment was purified by binding to glass beads (Vogelstein et al., Proc. Nat'l. Acad. Sci. USA, Vol. 76, p. 615 (1979)). The DNA fragments were cleaved with Sty I at nt 477 and end-labeled by fill-in with the Klenow fragment of DNA Polymerase I and $^{32}$P-dCTP. Following electrophoresis of the reaction mixture through a non-denaturing polyacrylamide gel, the 282 bp Sty I fragment (nt 477–758), labeled at the proximal end and containing codon 175, was eluted and purified by extraction with phenol and cloroform. A portion of the eluted DNA was cleaved with Hha I and the fragments separated by electrophoresis on a 6% sequencing gel. The presumptive mutation abolished the Hha I site normally present at codon 175 (GCGC at nt 522 to 525). Thus, Hha I cleavage of the PCR products from DNA of the normal cells of the patient providing Cx1 (FIG. 5, lanes 3 and 4) or from the tumor of another patient (lanes 5 and 6) produced only the 48 bp product expected if codon 175 was wild-type. In contrast, the PCR product from tumor Cx1 was not cleaved at nt 524 (corresponding to codon 175) and exhibited only a larger 66 bp fragment resulting from cleavage at a normal downstream Hha I site at nt 542. Analysis of the PCR product from paraffin embedded samples of the primary tumor and liver metastasis also exhibited the diagnostic 66 bp Hha I fragment indicating the presence of a mutation.

EXAMPLE 6

This example shows that five out of twenty-one carcinomas tested with the RNase protection method produced mRNA molecules with detectable sequence mismatches to the wild-type p53 RNA sequence.

Hybrids between a p53 anti-sense RNA probe and p53 mRNA should be cleaved by RNase A only at sequence mismatches. Although this method is not as definitive or as sensitive as sequencing, it allows rapid screening of a larger number of tumors. Twenty-one colorectal carcinomas (6 primary tumors and 15 cell lines) were examined with probes that included most of the p53 coding region.

Ten ug of cellular RNA was hybridized with radiolabeled anti-sense p53 RNA probe, and the hybrids digested with RNase A. A $^{32}$P-labelled RNA probe was generated in vitro from a p53 cDNA subclone in Bluescript (Stratagene Cloning Systems, La Jolla, Calif.). The probe included 561 nt of p53 mRNA coding sequence (nt 473–1034 relative to the translation start site) plus 60 nt derived from the vector.

Figure 6:
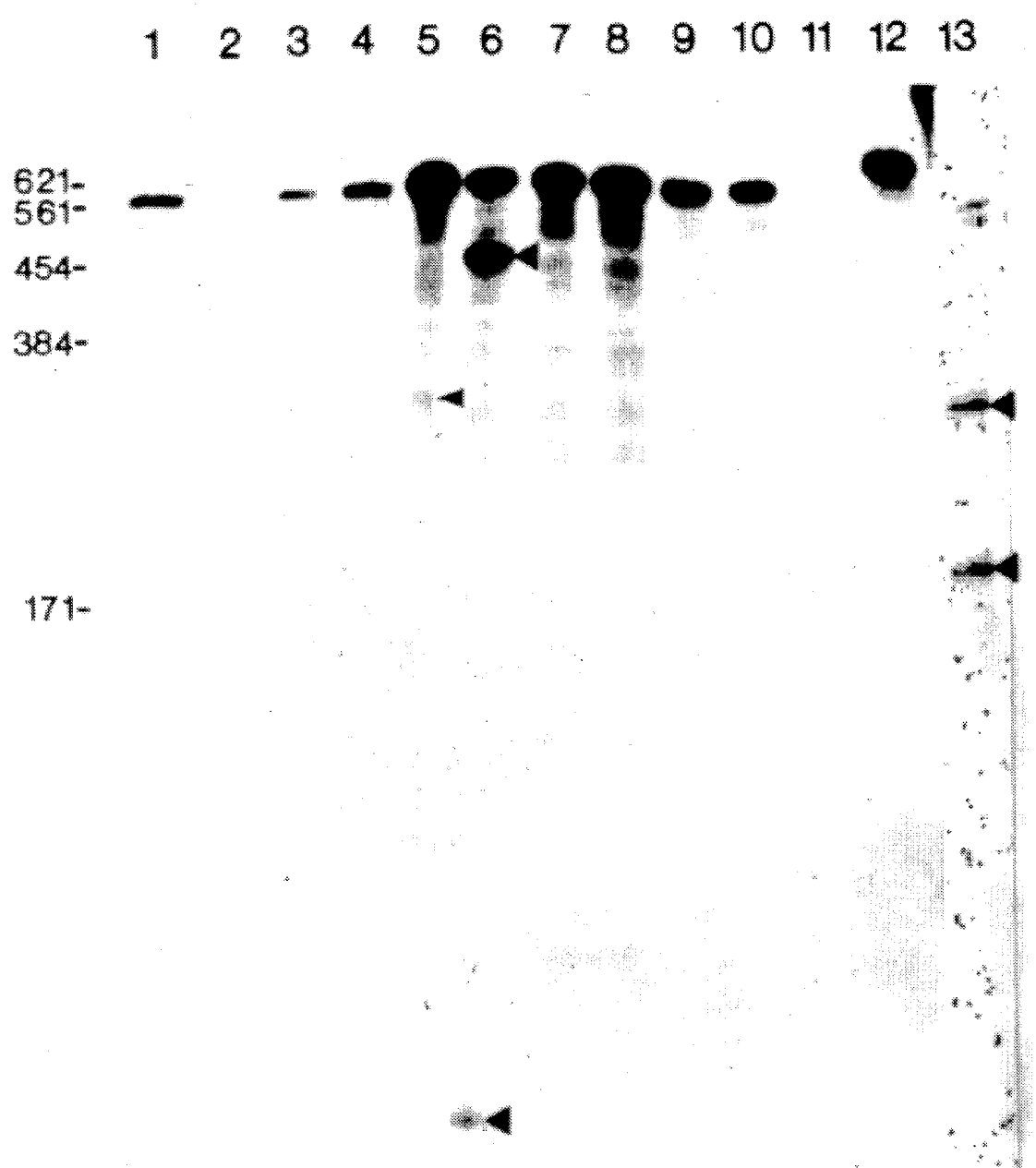
FIG. 6 depicts RNase protection analysis of p53 mRNA. Cellular RNA was hybridized with radiolabeled anti-sense p53 RNA probe, and the hybrids digested with RNase A. The RNA was derived from: lane 1: S115, carcinoma biopsy; lane 2: SW1417; lane 3: SW948; lane 4: RKO; lane 5: SW480; lane 6: RCA; lane 7: GEO; lane 8 FET; lane 9: xenograft Cx3; lane 10: normal colonic mucosa; lane 11: yeast tRNA; lane 12: probe alone (not RNase A digested); lane 13:SW1417 (long exposure). The fragments marked with arrowheads in lanes 5,6, and 13 were not present in the other samples.
Figure 7:
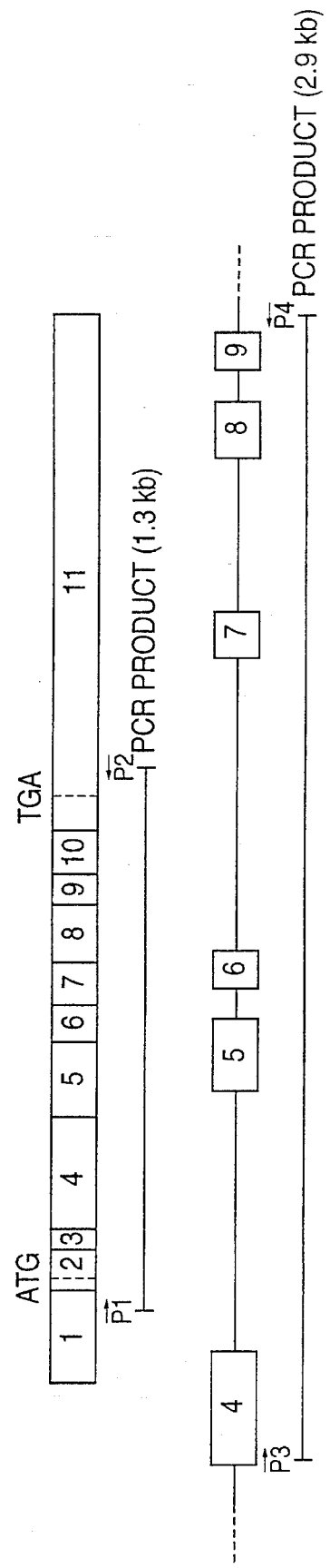
FIG. 7 diagrams the strategies used for amplification of p53 gene sequences. mRNA was used to generate a cDNA template for a polymerase chain reaction (PCR) employing primers P1 and P2 (top). The PCR product was 1.3 kb and included the entire coding region. Alternatively, total genomic DNA was used in a PCR reaction employing primers P3 and P4. The PCR product was 2.9 kb and included exons 4–9 (bottom). The numbered boxes indicate exons and the vertical dotted lines indicate the start (ATG) and stop (TGA) codons respectively.

The protected fragments were separated by electrophoresis through denaturing polyacrylamide gels; autoradiographs of the gels are presented in FIG. 6. The RNA was derived from: lane 1: S115, carcinoma biopsy; lane 2: SW1417; lane 3: SW948; lane 4: RKO; lane 5: SW480; lane 6: RCA; lane 7: GEO; lane 8: FET; lane 9: xenograft Cx3; lane 10: normal colonic mucosa; lane 11: yeast tRNA; lane 12: probe alone (not digested with RNase A); lane 13:SW1417 (long exposure). The fragments marked with arrowheads in lanes 5, 6 and 13 were not present in the other samples. The autoradiographic exposure time for lane 13 was 72 hours to allow adequate visualization of the new fragments; for all other lanes the exposure time was 10 hours.

The RNA from 5 carcinomas protected fragments of a different size than those seen with RNA from normal cells. In two cases, the new fragments were the major fragments detected (FIG. 6, lanes 6 and 13, arrowheads). In other cases, the new fragments were of minor intensity compared to the fully protected fragment (for example, SW480 in lane 5). Such partial cleavages are not unexpected; the mutations in Cx3 and Cx1 were not detected by the RNase protection method (data not shown) and it is known that the majority of RNA sequence mismatches are partially or totally resistant to RNaseA.

Using similar techniques, five additional colorectal cancers, two breast tumors and one lung tumor have been examined for p53 gene mutations. In all cases, point mutations of the p53 gene were observed.

EXAMPLE 7

This example demonstrates that a variety of types of tumors exhibit mutations in the p53 gene; that most tumors with allelic deletions of p53 have a mutation in the retained allele; that even some tumors with no p53 deletion have mutations in the p53 gene; and that the p53 mutations are clustered in four hot-spots on the gene.

A Variety of Tumors Carry p53 Mutations

We analyzed p53 sequences of tumors derived from the breast, lung, brain, colon, or mesenchyme. Tumors of these types have been previously shown to exhibit frequent deletions of chromosome 17p when studied by restriction fragment length polymorphism (RFLP) methods. To test for allelic deletions, tumor DNA samples were digested with HinfI and, following Southern transfer, hybridized sequentially to two probes (p144D6 (Kondoleon, et al., Nucleic Acids Res., vol. 15, p. 10605, 1987) and pYNZ22.1 (Nakamura, et al., Nucleic Acids Res., vol. 16, p. 5707, 1988)) detecting variable number of tandem repeat ("VNTR" or "mini-satellite") sequences. DNA samples from normal tissues exhibited two alleles with at least one of these probes in 29 of 31 different individuals tested. Because of this high degree of polymorphism, allelic loss could be assessed with greater than 95% certainty in cell lines and xenografts even when corresponding normal tissue was not available for comparison.

Nineteen tumors with allelic deletions of chromosome 17p were selected for sequence analysis. For tumor cell lines and for xenografts passaged in athymic nude mice, cDNA was generated from mRNA using oligo dT as a primer. A 1300 bp fragment including the entire p53 coding region was generated from the cDNA using PCR, and this fragment was cloned and sequenced in its entirety. For primary tumors, sufficient RNA was often not available for the first approach, and PCR was used to generate a 2.9 kb fragment from tumor DNA. This was the longest fragment that we could reproducibly amplify from the p53 locus, and included all of the exons found to contain mutations through the first approach.

RNA was purified using guanidinium isothiocyanate (Chomczynski, et al., Analytical Biochem., vol. 162, p. 156, 1987) and mRNA selected by binding to Messenger Affinity Paper (Amersham). cDNA was synthesized from 500–750 ng of mRNA using oligo dT as a primer. The oligo dT primer was removed by isopropanol precipitation; 10 ug of tRNA and sodium perchlorate (to a final aqueous concentration of 0.5M) were added to the reaction, and this was followed by addition of ½ volume of isopropanol (Kinzler, et al, Nucleic Acids Res., vol. 17, p. 3645, 1989; Haymerle, et al., Nucleic Acids Res., vol. 14, p. 8615, 1986). The cDNA was pelleted by centrifugation for 15 min. at room temperature and used in a 50 ul PCR reaction consisting of 35 cycles of 93° (1 minute), 58° (1 minute), and 70° (2 minutes). Two ug of genomic DNA was used in a 200 ul PCR reaction consisting of 30 cycles at 95° (1 minute), 58° (1 minute), and 70° (4 minutes). PCR reactions contained magnesium chloride at a final concentration of 2 mM. The primers used were P1: 5'-GGAATTCCACGACGGTGACACG-3';
P2: 5'-GGAATTCAAAATGGCAGGGGAGGG-3';
P3: 5'-GTAGGAATTCGTCCCAAGCAATGGATGAT-3';
P4: 5-CATCGAATTCTGGAAACTTTCCACTTGAT-3'.

All primers had extraneous nucleotides comprising EcoRI sites at their 5' ends to facilitate cloning. The PCR products were digest with EcoRI, fractionated by electrophoresis, and following purification from agarose, ligated to EcoRI digested Bluescript vectors (Statagene). Individual clones were sequenced with primers derived from the p53 coding and intron sequences (Buchman, et al., Gene, vol. 70, p. 245, 1988) using T7 polymerase and the TDMN sequencing method described in Del Sal, et al., Biotech., vol. 7, p. 514, 1989.

Thirteen of the tumors were found to contain a single missense mutation; two tumors each contained two mutations; one tumor contained a frame-shift mutation at codon 293; and no mutation was detected in four tumors (Table 1). The PCR reaction is known to be associated with a relatively high rate of base misincorporation (Saiki, et al. Science, vol. 239, p. 487, 1988), and we confirmed this observation by noting several sequence variants (13 out of 34,000 bp sequenced) in individual clones that were not reproducibly present in other PCR reactions from the same tumor sample. All of the mutations listed in Table 1 were confirmed by performing a second PCR reaction and re-sequencing the products en masse as described below.

TABLE I p53 GENE MUTATIONS IN HUMAN TUMORS

| Tumor # | Tumor Name | Tumor Type[a] | Tumor Cells Tested[b] | # of 17p Alleles[c] | Codon | Nucleotide | Amino Acid |
|---|---|---|---|---|---|---|---|
| 1 | D263 | BRAIN | B, X | 1 | 175 | GCG—CAC | Arg—His |
| 2 | D274 | BRAIN | X | 1 | 273 | GCT—TGT | Arg—Cys |
| 3 | D303 | BRAIN | B, X | 1 | 216 | GTG—ATG | Val—Met |
| 4 | D317 | BRAIN | B, X | 1 | 272 | GTG—ATG | Val—Met |
| 5 | D247 | BRAIN | C | 1 | NONE DETECTED | | |
| 6 | MDA 468 | BREAST | C | 1 | 273 | CGT—CAT | Arg—His |
| 7 | T470 | BREAST | C | 1 | 194 | CTT—TTT | Leu—Phe |
| 8 | BT123 | BREAST | B | 1 | NONE DETECTED | | |
| 9 | 1012 | LUNG | B | 1 | 293 | DELETED a G | Frameshift |
| 10 | 5855 | LUNG | B | 1 | NONE DETECTED | | |
| 11 | H231 | LUNG | C | 2 | 134 | TTT—TTA | Phe—Leu |
| 12 | 88-3/14 | NFS | B, C | 1 | 179 | CAT—TAT | His—Tyr |

TABLE I-continued p53 GENE MUTATIONS IN HUMAN TUMORS

| Tumor # | Tumor Name | Tumor Type[a] | Tumor Cells Tested[b] | # of 17p Alleles[c] | MUTATION Codon | MUTATION Nucleotide | MUTATION Amino Acid |
|---|---|---|---|---|---|---|---|
| 13 | Cx4A | COLON | B, X | 1 | 239 | AAC—AGC | Asn—Ser |
| 14 | Cx5A | COLON | X | 1 | 248 | CGG—TGG | Arg—Trp |
| 15 | Cx6A | COLON | X | 1 | 132 | AAG—AAC | Lys—Asn |
|  |  |  |  |  | 133 | ATG—TTG | Met—Leu |
| 16 | Cx7A | COLON | B, X | 2 | 281 | GAC—GGC | Asp—Gly |
| 17 | CX19A | COLON | X | 2 |  | NONE DETECTED |  |
| 18 | Cx20A | COLON | B, X | 1 | 175 | CGC—CAC | Arg—His |
| 19 | Cx22A | COLON | X | 1 | 175 | CGC—CAC | Arg—His |
| 20 | Cx26A | COLON | X | 1 | 141 | TGC—TAC | Cys—Tyr |
| 21 | SW480 | COLON | C | 1 | 273 | CGT—CAT | Arg—His |
|  |  |  |  |  | 309 | CCC—TCC | Pro—Ser |
| 22 | SW837 | COLON | C | 1 | 248 | CGG—TGG | Arg—Trp |

[a]The brain tumors were glioblastoma multiforme; the colon and breast tumors were adenocarcinomas, the NFS tumor was a neurofibrosarcoma developing in a patient with type I neurofibromatosis; H231 was a small cell carcinoma of the lung, and the other two lung tumors were non-small cell carcinomas.
[b]B = tumor biopsy; C = cell line passaged in vitro; X = xenograft derived from biopsy, passaged in athymic nude mice. Whenever two sources of tumor cells are listed, both contained the indicated mutation.
[c]The number of alleles was determined by RFLP analysis as described in the text.

Six p53 Mutations are Somatic Mutations

Two observations indicated that the nucleotide substitutions described in Table I represented somatic mutations. First, none of these presumptive mutations have been observed in the sequences of human p53 genes derived from normal cells, SV40 transformed fibroblasts, or lymphoblastoid cell lines (Zakut-Houri, et al., EMBO, vol. 4, p. 1251, 1985; Lamb, et al., Mol. Cell. Biol., vol. 6, p. 1379, 1986; Matlashewski, Mol. Cell Biol., vol. 7, p. 961, 1987; Harris, et al., Mol. Cell. Biol., vol. 6, p. 4650, 1986; Matlashewski, et al., EMBO J., vol. 3, p. 3257, 1984 and our unpublished data). Second, in 6 cases (tumors #2, 3, 9, 12, 13, 16), normal tissue from the patients whose tumors are described in Table I were available for study. To test for the presence of the presumptive mutations (in the heterozygous state) in the germline of these patients, a strategy was devised which employed both PCR and cloning. Although direct sequencing of PCR products has been shown to be possible by several methods, we found that none of the published methods could be reproducibly applied to all parts of the p53 coding region. To circumvent this difficulty, we cloned the PCR products into a phagemid vector and used the DNA pooled from $10^3$ to $10^4$ independent phage clones as a template for DNA sequencing.

PCR reactions were carried out as described above and the reaction products digested with EcoRI. The entire reaction was ligated to 0.25 ug of lambda ZAP phage vector arms (Stratagene) and packaged using ¼ of a GIGA-PACK extract (Stratagene). E. coli BB4 cells were then infected, and $10^3$–$10^4$ phage clones plated on a 7 cm petri dish. The lambda ZAP vector contains the sequences for a phagemid into which the PCR inserts were cloned, and single stranded DNA phage can be rescued from the lambda phage clones using a helper phage (Short, et al., Nucleic Acids Res., vol. 16, p. 7583, 1988). An overnight culture of XL-I Blue cells (Stratagene) was grown in 0.4% maltose and resuspended in 1.5 volumes of 10 mM magnesium sulfate. Phages were eluted from the 7 cm dish in 5 ml phage dilution buffer (100 mM sodium chloride, 10 mM magnesium sulfate, 20 mM Tris, ph 7.5, 0.02% gelatin) for 2 hours at room temperature with gentle agitation. Fifty ul of eluate was used to infect 200 ul of XL-I Blue cells (Stratagene) in the presence of 1 ul helper phage R408 ($10^{11}$ PFU/ml). After 15 min. at 37°, 5 ml of 2 x YT broth was added and the culture shaken for 3 hours at 37°, then heated to 70° for 20 min. Cell debris was pelleted at 3000 g for 5 min., and 10 ul of the supernatant, containing single-stranded DNA phage, was used to infect 200 ul of XL-1 Blue cells prepared as described above. After 15 min. at 37°, 100 ul of the mixture (containing over $10^4$ clones determined by titration on XL-1 Blue cells) was inoculated into 50 ml L-Broth and shaken overnight at 37°. Double-stranded DNA was isolated by a rapid alkaline lysis technique (Birnboim, et al., Nucleic Acids Res., vol. 7, p. 1513, 1979) and sequenced as described above. The primer used for sequencing in panels 1 and 2 was 5'-GAGGCAAG-CAGAGGTGG-3'. The primer used for sequencing in panels 3 and 4 was 5'-TGGTAATCTACTGGGACG-3'.

This procedure resulted in sequence data quality as high as that produced using individual plasmid DNA clones as templates, and was used to demonstrate that in each of the six cases noted above, the mutations in the tumor DNA were not present in the germline of the patient.

Two Tumors with No Allelic Loss of p53 Carried D53 Mutations

The data described above indicated that most tumors with one 17p allele contained a mutation of the p53 gene in the remaining allele. To begin to assess the status of tumors which had not lost a 17p allele, we examined cDNA clones from three such tumors. In each case, two cDNA clones derived from PCR products, generated as described above were sequenced. In one case (tumor #11), both clones contained a single point mutation at codon 134 (Table I). In the second case (tumor #16), one clone contained a point mutation at codon 281 and one clone was wild type. In the third case (tumor #17), both clones were wild type. To assess the relative expression levels of the mutant alleles, the sequencing strategy employing pooled phage clones was utilized with cDNA from tumor mRNA as a template. In tumor number #11, only the mutant allele was expressed (data not shown); in tumor #16, the mutant and wild type alleles were expressed at approximately equal levels.

The p53 Mutations are Clustered Along the Gene

Altogether, 20 point mutations (19 missense, 1 frameshift) were identified in the present example. These are mapped in FIG. 8, together with the two human p53 gene missense mutations previously described (Baker, et al., Science, vol. 244, p. 217, 1989). Several features are notable. Although the sample size is limited, the mutations tended to be clustered in four hotspots which accounted for 86% of the 21 missense mutations (5 mutations in region A, codons 132–143; five mutations in region B, codons 174–179; 3 mutations in region C, codons 236–248; 5 mutations in region D, codons 272–281). There have been two missense mutations identified in murine tumor cells, both in the carcinogen-induced fibrosarcoma cell line Meth A: one allele contained a mutation in region A, and the other contained one mutation in region C and one mutation in region D (Finlay, et al., Mol. Cell. Biol., vol. 8, p. 531, 1988; Eliyahu, et al., Oncogene, vol. 3, p. 313, 1988). Interestingly, the four hotspots for in vivo mutation coincided exactly with the four most highly conserved regions of the p53 gene, previously identified (Soussi, et al., Oncogene, vol. 1, p. 71, 1987). Of the 41 amino acids contained within regions A–D, 93% are identical in the wild-type p53 genes of amphibian, avian, and mammalian species, compared to a conservation of only 51–57% over the entire p53 coding sequence. The clustering of mutations and evolutionary conservation of regions A–D suggest that they play a particularly important role in mediating the normal function of the p53 gene product.

We claim:

1. A method of determining neoplasia of a tissue of a human, comprising:

obtaining a first human tissue suspected of being neoplastic, comparing p53 genes or p53 transcripts in said first human tissue to wild-type p53 genes or wild-type p53 transcripts having a size of about 2.8 kb, said wild-type p53 genes or transcripts being defined by their presence in normal human tissues, an observed difference between p53 genes or p53 transcripts in the first tissue of said human and wild-type indicating neoplasia of the tissue.

2. The method of claim 1 wherein loss of wild-type transcripts having a size of about 2.8 kb is detected.

3. The method of claim 1 wherein the loss of wild-type p53 genes is detected by sequencing all or part of the p53 gene using polymerase chain reaction.

4. The method of claim 1 wherein the loss of wild-type p53 genes is detected by identifying a mismatch between molecules (1) a p53 gene or p53 mRNA in said tissue and (2) a nucleic acid probe complementary to the human wild-type p53 gene, when molecules (1) and (2) are hybridized to each other to form a duplex.

5. The method of claim 4 wherein the nucleic acid probe is a riboprobe.

6. The method of claim 4 wherein the nucleic acid probe is a DNA probe.

7. The method of claim 4 wherein the mismatch is identified by enzymatic cleavage.

8. The method of claim 4 wherein the mismatch is identified by chemical cleavage.

9. The method of claim 7 wherein the enzymatic cleavage is selected from the group consisting of RNase A and S1 nuclease.

10. The method of claim 4 wherein the mismatch is identified by observing a shift in electrophoretic mobility of the duplex relative to the mobility of a duplex formed when molecule (2) is hybridized to a wild-type p53 gene or p53 mRNA.

11. The method of claim 1 wherein the loss of wild-type p53 genes is detected by amplification of p53 gene sequences and hybridization of the amplified p53 sequences to nucleic acid probes which are complementary to mutant p53 alleles.

12. The method of claim 1 wherein the loss of wild-type p53 genes is detected by molecular cloning and sequencing all or part of the p53 gene.

13. The method of claim 1 wherein the detection of loss of wild-type p53 genes comprises screening for a point mutation.

14. The method of claim 13 wherein the point mutation is a missense mutation.

15. The method of claim 1 wherein the detection of loss of wild-type p53 genes comprises screening for a frameshift mutation.

16. The method of claim 1 wherein the detection of loss of wild-type p53 genes comprises screening for a deletion mutation.

17. The method of claim 1 wherein the detection of loss of wild-type p53 genes comprises screening for a point mutation and screening for a deletion mutation.

18. The method of claim 1 wherein the neoplastic tissue is selected from the group consisting of: lung, breast, brain, colorectal, bladder, prostate, liver and stomach tumors.

19. The method of claim 18 wherein the neoplastic tissue is selected from the group consisting of: lung, breast, and colorectal tumors.

20. The method of claim 19 wherein the neoplastic tissue is a colorectal carinoma.

21. An allele-specific nucleic acid probe consisting of the nucleic acid sequence of a region of a human mutant p53 gene or its ribonucleotide equivalent, said region containing a mutation.

22. The probe of claim 21 which is a riboprobe.

23. The probe of claim 21 which is a DNA probe.

24. A method of detecting the presence of a neoplastic tissue in a human, comprising:

obtaining a body sample isolated from a human;

comparing p53 genes or p53 transcripts in the body sample to a wild-type p53 gene or wild-type p53 transcripts having a size of about 2.8 kb, said wild-type p53 gene or transcripts being defined by their presence in normal human tissues, an observed difference between the p53 genes or p53 transcripts in the body sample and wild-type indicating the presence of a neoplastic tissue in the human.

25. The method of claim 24 wherein said body sample is selected from the group consisting of serum, stool, urine and sputum.

26. A method of detecting genetic predisposition to cancer in a human, comprising:

extracting DNA from a human sample selected from the group consisting of blood and fetal tissue;

comparing a p53 gene in said DNA to a wild-type p53 gene, said wild-type p53 gene being defined by its presence in normal human tissues, an observed difference between the p53 genes indicating a predisposition to cancer in the human.

27. A method of determining neoplasia of a tissue of a human, comprising:

obtaining a first human tissue suspected of being neoplastic;

comparing p53 genes or p53 transcripts in the first human tissue to wild-type p53 genes or wild-type p53 transcripts having a size of about 2.8 kb, said wild-type p53 genes or transcripts being defined by their presence in normal tissues of said human, an observed difference between the p53 genes or p53 transcripts indicating neoplasia.

28. The probe of claim 21 wherein the mutation is contained within a codon selected from the group consisting of: 132–143, 174–179, 236–248, and 272–281.

29. The probe of claim 21 wherein the mutation is contained within the amino acid coding region of said p53 gene sequence.

30. The method of claim 26 wherein a mutation is a codon selected from the group consisting of: 132–143, 174–179, 236–248, and 272–281 is detected.

31. The method of claim 27 wherein a mutation in a codon selected from the group consisting of: 132–143, 174–179, 236–248, and 272–281 is detected.

32. The method of claim 26 wherein a mutation in the coding region which alters the wild-type amino acid sequence is detected.

33. The method of claim 27 wherein a mutation in the coding region which alters the wild-type amino acid sequence is detected.

34. The probe of claim 28 wherein the mutation substitutes an alanine at amino acid 143 of p53.

35. The probe of claim 28 wherein the mutation substitutes a histidine at amino acid 175 of p53.

36. The probe of claim 28 wherein the mutation substitutes a cysteine at amino acid 273 of p53.

37. The probe of claim 28 wherein the mutation substitutes a methionine at amino acid 216 of p53.

38. The probe of claim 28 wherein the mutation substitutes a methionine at amino acid 272 of p53.

39. The probe of claim 28 wherein the mutation substitutes a histidine at amino acid 273 of p53.

40. The probe of claim 28 wherein the mutation substitutes a phenylalanine at amino acid 194 of p53.

41. The probe of claim 28 wherein the mutation substitutes a leucine at amino acid 134 of p53.

42. The probe of claim 28 wherein the mutation substitutes a tyrosine at amino acid 179 of p53.

43. The probe of claim 28 wherein the mutation substitutes a serine at amino acid 239 of p53.

44. The probe of claim 28 wherein the mutation substitutes a tryptophan at amino acid 248 of p53.

45. The probe of claim 28 wherein the mutation substitutes an asparagine amino acid 132 of p53.

46. The probe of claim 28 wherein the mutation substitutes a leucine at amino acid 133 of p53.

47. The probe of claim 28 wherein the mutation substitutes a glycine at amino acid 281 of p53.

48. The probe of claim 28 wherein the mutation substitutes a tyrosine at amino acid 141 of p53.

49. The probe of claim 28 wherein the mutation substitutes a serine at amino acid 309 of p53.

50. The probe of claim 28 wherein the mutation is a deletion of a guanine in codon 293 of human p53.

51. The method of claim 1 comprising the step of:

comparing p53 genes or p53 transcripts in said first human tissue to p53 genes or p53 transcripts in a normal tissue of said human, an observed difference between p53 genes or p53 transcripts, in the two tissues of said human indicating neoplasia of the first tissue.

52. The method of claim 24 comprising the step of:

comparing p53 genes or p53 transcripts, in said body sample to p53 genes or p53 transcripts in a normal tissue of said human, an observed difference between p53 genes or p53 transcripts in the body sample and the normal tissue of said human indicating neoplasia or a tissue in said human.

53. The method of claim 27 comprising the step of:

comparing p53 genes or p53 transcripts, in said first human tissue to p53 genes or p53 transcripts, in a normal tissue of said human, an observed difference between p53 genes or p53 transcripts, in the two tissues of said human indicating neoplasia of the first tissue.

54. A kit for determination of the nucleotide sequence of a p53 gene by polymerase chain reaction, comprising:

a pair of single stranded DNA primers, said pair allowing synthesis of wild-type p53 gene coding sequences; and an allele-specific nucleic acid probe consisting of the nucleic acid sequence of a region of a human mutant p53 gene or its ribonucleotide equivalent, said region containing a mutation.

55. The kit of claim 54 wherein the primers have restriction enzyme sites at each 5' end.

56. A kit for determination of the nucleotide sequence of a p53 gene by polymerase chain reaction, comprising:

a set of pairs of single stranded DNA primers, said set allowing synthesis of all nucleotides of the wild-type p53 gene coding sequences; and an allele-specific nucleic acid probe consisting of the nucleic acid sequence of a region of a human mutant p53 gene or its ribonucleotide equivalent, said region containing a mutation.

57. The kit of claim 56 wherein the primers have restriction enzyme sites at each 5' end.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
    ( A ) LENGTH: 412 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens
    ( F ) TISSUE TYPE: placenta ( v i i i ) POSITION IN GENOME:
    ( A ) CHROMOSOME/SEGMENT: exon 1

( x ) PUBLICATION INFORMATION:
    ( A ) AUTHORS: Buchman, V. L.
    ( B ) TITLE: A variation in the structure of the
        protein- coding region of the human p53 gene
    ( C ) JOURNAL: Gene
    ( D ) VOLUME: 70
    ( F ) PAGES: 245-252
    ( G ) DATE: 1988

( x i ) SEQUENCE DESCRIPTION: SEQ ID NO:1:

| | | | | | | |
|---|---|---|---|---|---|---|
| GGATTCCTCC | AAAATGATTT | CCACCAATTC | TGCCCTCACA | GCTCTGGCTT | GCAGAATTTT | 60 |
| CCACCCCAAA | ATGTTAGTAT | CTACGGCACC | AGGTCGGCGA | GAATCCTGAC | TCTGCACCCT | 120 |
| CCTCCCCAAC | TCCATTTCCT | TTGCTTCCTC | CGGCAGGCGG | ATTACTTGCC | CTTACTTGTC | 180 |
| ATGGCGACTG | TCCAGCTTTG | TGCCAGGAGC | CTCGCAGGGG | TTGATGGGAT | TGGGGTTTTC | 240 |
| CCCTCCCATG | TGCTCAAGAC | TGGCGCTAAA | AGTTTTGAGC | TTCTCAAAAG | TCTAGAGCCA | 300 |
| CCGTCCAGGG | AGCAGGTAGC | TGCTGGGCTC | CGGGGACACT | TTGCGTTCGG | GCTGGGAGCG | 360 |
| TGCTTTCCAC | GACGGTGACA | CGCTTCCCTG | GATTGGGTAA | GCTCCTGACT | GA | 412 |

( 2 ) INFORMATION FOR SEQ ID NO:2:

( i ) SEQUENCE CHARACTERISTICS:
    ( A ) LENGTH: 133 base pairs
    ( B ) TYPE: nucleic acid
    ( C ) STRANDEDNESS: double
    ( D ) TOPOLOGY: linear ( i i ) MOLECULE TYPE: cDNA ( v i ) ORIGINAL SOURCE:

(A) ORGANISM: Homo sapiens (viii) POSITION IN GENOME:
    (A) CHROMOSOME/SEGMENT: exon 2

(x) PUBLICATION INFORMATION:
    (A) AUTHORS: Buchman, V. L.
    (B) TITLE: A variation in the structure of the protein- coding region of the human p53 gene
    (C) JOURNAL: Gene
    (D) VOLUME: 70
    (F) PAGES: 245-252
    (G) DATE: 1988

(xi) SEQUENCE DESCRIPTION: SEQ ID NO:2:

```
TGGATCCTCT TGCAGCAGCC AGACTGCCTT CCGGGTCACT GCCATGGAGG AGCCGCAGTC    60
AGATCCTAGC GTCGAGCCCC CTCTGAGTCA GGAAACATTT TCAGACCTAT GGAAACTGTG   120
AGTGGATCCA TTG                                                     133
```

(2) INFORMATION FOR SEQ ID NO:3:

(i) SEQUENCE CHARACTERISTICS:
        (A) LENGTH: 52 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: exon 3

(x) PUBLICATION INFORMATION:
        (A) AUTHORS: Buchman, V. L.
        (B) TITLE: A variation in the structure of the protein- coding region of the human p53 gene
        (C) JOURNAL: Gene
        (D) VOLUME: 70
        (F) PAGES: 245-252
        (G) DATE: 1988

(xi) SEQUENCE DESCRIPTION: SEQ ID NO:3:

```
GCTCTTGACT TTCAGACTTC CTGAAAACAA CGTTCTGGTA AGGACAAGGG TT            52
```

(2) INFORMATION FOR SEQ ID NO:4:

(i) SEQUENCE CHARACTERISTICS:
        (A) LENGTH: 311 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: exon 4

(x) PUBLICATION INFORMATION:
        (A) AUTHORS: Buchman, V. L.
        (B) TITLE: A variation in the sturcture of the protein-coding region of the human p53 gene
(C) JOURNAL: Gene
(D) VOLUME: 70
(F) PAGES: 245-252
(G) DATE: 1988

(xi) SEQUENCE DESCRIPTION: SEQ ID NO:4:

| | | | | | | |
|---|---|---|---|---|---|---|
| TTTTCACCCA | TCTACAGTCC | CCCTTGCCGT | CCCAAGCAAT | GGATGATTTG | ATGCTGTCCC | 60 |
| CGGACGATAT | TGAACAATGG | TTCACTGAAG | ACCCAGGTCC | AGATGAAGCT | CCCAGAATGC | 120 |
| CAGAGGCTGC | TCCCCCCGTG | GCCCCTGCAC | CAGCAGCTCC | TACACCGGCG | GCCCCTGCAC | 180 |
| CAGCCCCCTC | CTGGCCCCTG | TCATCTTCTG | TCCCTTCCCA | GAAAACCTAC | CAGGGCAGCT | 240 |
| ACGGTTTCCG | TCTGGGCTTC | TTGCATTCTG | GGACAGCCAA | GTCTGTGACT | TGCACGGTCA | 300 |
| GTTGCCCTGA | G | | | | | 311 |

(2) INFORMATION FOR SEQ ID NO:5:

(i) SEQUENCE CHARACTERISTICS:
      (A) LENGTH: 214 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (viii) POSITION IN GENOME:
      (A) CHROMOSOME/SEGMENT: exon 5

(x) PUBLICATION INFORMATION:
      (A) AUTHORS: Buchman, V. L.
      (B) TITLE: A variation in the structure of the
             protein-coding region of the human p53 gene
      (C) JOURNAL: Gene
      (D) VOLUME: 70
      (F) PAGES: 245-252
      (G) DATE: 1988

(xi) SEQUENCE DESCRIPTION: SEQ ID NO:5:

| | | | | | | |
|---|---|---|---|---|---|---|
| TTCCTCTTCC | TGCAGTACTC | CCCTGCCCTC | AACAAGATGT | TTTGCCAACT | GGCCAAGACC | 60 |
| TGCCCTGTGC | AGCTGTGGGT | TGATTCCACA | CCCCCGCCCG | GCACCCGCGT | CCGCGCCATG | 120 |
| GCCATCTACA | AGCAGTCACA | GCACATGACG | GAGGTTGTGA | GGCGCTGCCC | CCACCATGAG | 180 |
| CGCTGCTCAG | ATAGCGATGG | TGAGCAGCTG | GGGC | | | 214 |

(2) INFORMATION FOR SEQ ID NO:6:

(i) SEQUENCE CHARACTERISTICS:
      (A) LENGTH: 144 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (viii) POSITION IN GENOME:
      (A) CHROMOSOME/SEGMENT: exon 6

( x ) PUBLICATION INFORMATION:
    ( A ) AUTHORS: Buchman, et al.
    ( C ) JOURNAL: Gene
    ( D ) VOLUME: 70
    ( F ) PAGES: 245-252
    ( G ) DATE: 1988

( x i ) SEQUENCE DESCRIPTION: SEQ ID NO:6:

```
CACTGATTGC TCTTAGGTCT GGCCCCTCCT CAGCATCTTA TCCGAGTGGA AGGAAATTTG     60
CGTGTGGAGT ATTTGGATGA CAGAAACACT TTTCGACATA GTGTGGTGGT GCCCTATGAG    120
CCGCCTGAGG TCTGGTTTGC AACT                                          144
```

( 2 ) INFORMATION FOR SEQ ID NO:7:

( i ) SEQUENCE CHARACTERISTICS:
       ( A ) LENGTH: 139 base pairs
       ( B ) TYPE: nucleic acid
       ( C ) STRANDEDNESS: double
       ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
       ( A ) ORGANISM: Homo sapiens ( v i i i ) POSITION IN GENOME:
       ( A ) CHROMOSOME/SEGMENT: exon 7

( x ) PUBLICATION INFORMATION:
       ( A ) AUTHORS: Buchman, et al.
       ( C ) JOURNAL: Gene
       ( D ) VOLUME: 70
       ( F ) PAGES: 245-252
       ( G ) DATE: 1988

( x i ) SEQUENCE DESCRIPTION: SEQ ID NO:7:

```
GTGTTGTCTC CTAGGTTGGC TCTGACTGTA CCACCATCCA CTACAACTAC ATGTGTAACA     60
GTTCCTGCAT GGGCGGCATG AACCGGAGGC CCATCCTCAC CATCATCACA CTGGAAGACT    120
CCAGGTCAGG AGCCACTTG                                                139
```

( 2 ) INFORMATION FOR SEQ ID NO:8:

( i ) SEQUENCE CHARACTERISTICS:
       ( A ) LENGTH: 166 base pairs
       ( B ) TYPE: nucleic acid
       ( C ) STRANDEDNESS: double
       ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
       ( A ) ORGANISM: Homo sapiens ( v i i i ) POSITION IN GENOME:
       ( A ) CHROMOSOME/SEGMENT: exon 8

( x ) PUBLICATION INFORMATION:
       ( A ) AUTHORS: Buchman, et al.
       ( C ) JOURNAL: Gene
       ( D ) VOLUME: 70
       ( F ) PAGES: 245-252
       ( G ) DATE: 1988

( x i ) SEQUENCE DESCRIPTION: SEQ ID NO:8:

CCTATCCTGA GTAGTGGTAA TCTACTGGGA CGGAACAGCT TTGAGGTGCG TGTTTGTGCC      60

TGTCCTGGGA GAGACCGGCG CACAGAGGAA GAGAATCTCC GCAAGAAAGG GGAGCCTCAC     120

CACGAGCTGC CCCCAGGGAG CACTAAGCGA GGTAAGCAAG CAGGAC                   166

( 2 ) INFORMATION FOR SEQ ID NO:9:

( i ) SEQUENCE CHARACTERISTICS:
        ( A ) LENGTH: 104 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( A ) CHROMOSOME/SEGMENT: exon 9

( x ) PUBLICATION INFORMATION:
        ( A ) AUTHORS: Buchman, et al.
        ( C ) JOURNAL: Gene
        ( D ) VOLUME: 70
        ( F ) PAGES: 245-252
        ( G ) DATE: 1988

( x i ) SEQUENCE DESCRIPTION: SEQ ID NO:9:

TTGCCTCTTT CCTAGCACTG CCCAACAACA CCAGCTCCTC TCCCCAGCCA AAGAAGAAAC      60

CACTGGATGG AGAATATTTC ACCCTTCAGG TACTAAGTCT TGGG                     104

( 2 ) INFORMATION FOR SEQ ID NO:10:

( i ) SEQUENCE CHARACTERISTICS:
        ( A ) LENGTH: 136 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( A ) CHROMOSOME/SEGMENT: exon 10

( x ) PUBLICATION INFORMATION:
        ( A ) AUTHORS: Buchman, et al.
        ( C ) JOURNAL: Gene
        ( D ) VOLUME: 70
        ( F ) PAGES: 245-252
        ( G ) DATE: 1988

( x i ) SEQUENCE DESCRIPTION: SEQ ID NO:10:

CTCTGTTGCT GCAGATCCGT GGGCGTGAGC GCTTCGAGAT GTTCCGAGAG CTGAATGAGG      60

CCTTGGAACT CAAGGATGCC CAGGCTGGGA AGGAGCCAGG GGGGAGCAGG GCTCACTCCA     120

GGTGAGTGAC CTCAGC                                                    136

( 2 ) INFORMATION FOR SEQ ID NO:11:

( i ) SEQUENCE CHARACTERISTICS:
    ( A ) LENGTH: 1316 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( v i i i ) POSITION IN GENOME:
    ( A ) CHROMOSOME/SEGMENT: exon 11

( x ) PUBLICATION INFORMATION:
    ( A ) AUTHORS: Buchman, et al.
    ( C ) JOURNAL: Gene
    ( D ) VOLUME: 70
    ( F ) PAGES: 245-252
    ( G ) DATE: 1988

( x i ) SEQUENCE DESCRIPTION: SEQ ID NO:11:

```
GCTTCTGTCT CCTACAGCCA CCTGAAGTCC AAAAAGGGTC AGTCTACCTC CCGCCATAAA      60
AAACTCATGT TCAAGACAGA AGGGCCTGAC TCAGACTGAC ATTCTCCACT TCTTGTTCCC     120
CACTGACAGC CTCCCTCCCC CATCTCTCCC TCCCCTGCCA TTTTGGGTTT TGGGTCTTTG     180
AACCCTTGCT TGCAATAGGT GTGCGTCAGA AGCACCCAGG ACTTCCATTT GCTTTGTCCC     240
GGGGCTCCAC TGAACAAGTT GGCCTGCACT GGTGTTTTGT TGTGGGGAGG AGGATGGGA      300
GTAGGACATA CCAGCTTAGA TTTTAAGGTT TTTACTGTGA GGGATGTTTG GGAGATGTAA     360
GAAATGTTCT TGCAGTTAAG GGTTAGTTTA CAATCAGCCA CATTCTAGGT AGGGGCCCAC     420
TTCACCGTAC TAACCAGGGA AGCTGTCCCT CATGTTGAAT TTTCTCTAAC TTCAAGGCCC     480
ATATCTGTGA AATGCTGGCA TTTGCACCTA CCTCACAGAG TGCATTGTGA GGGTTAATGA     540
AATAATGTAC ATCTGGCCTT GAAACCACCT TTTATTACAT GGGTCTAAA  ACTTGACCCC     600
CTTGAGGGTG CCTGTTCCCT CTCCCTCTCC CTGTTGGCTG GTGGGTTGGT AGTTTCTACA     660
GTTGGGCAGC TGGTTAGGTA GAGGGAGTTG TCAAGTCTTG CTGGCCCAGC CAAACCCTGT     720
CTGACAACCT CTTGGTCCAC CTTAGTACCT AAAAGGAAAT CTCACCCCAT CCCACACCCT     780
GGAGGATTTC ATCTCTTGTA TATGATGATC TGGATCCACC AAGACTTGTT TTATGCTCAG     840
GGTCAATTTC TTTTTTCTTT TTTTTTTTT  TTTTTCTTTT TCTTTGAGAC TGGGTCTCGC     900
TTTGTTGCCC AGGCTGGAGT GGAGTGGCGT GATCTTGGCT TACTGCAGCC TTTGCCTCCC     960
CGGCTCGAGC AGTCCTGCCT CAGCCTCCGG AGTAGCTGGG ACCACAGGTT CATGCCACCA    1020
TGGCCAGCCA ACTTTTGCAT GTTTGTAGA  GATGGGGTCT CACAGTGTTG CCCAGGCTGG    1080
TCTCAAACTC CTGGGCTCAG GCGATCCACC TGTCTCAGCC TCCCAGAGTG CTGGGATTAC    1140
AATTGTGAGC CACCACGTCC AGCTGGAAGG GTCAACATCT TTTACATTCT GCAAGCACAT    1200
CTGCATTTTC ACCCCACCCT TCCCTCCTT  CTCCCTTTTT ATATCCCATT TTTATATCGA    1260
TCTCTTATTT TACAATAAAA CTTTGCTGCC ACCTGTGTGT CTGAGGGGTG AACGCC        1316
```

( 2 ) INFORMATION FOR SEQ ID NO:12:

( i ) SEQUENCE CHARACTERISTICS:
        ( A ) LENGTH: 1307 base pairs
        ( B ) TYPE: nucleic acid
        ( C ) STRANDEDNESS: double
        ( D ) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Homo sapiens (viii) POSITION IN GENOME:
(B) MAP POSITION: 17p13.1

(x) PUBLICATION INFORMATION:
(A) AUTHORS: Harris, N.
(B) TITLE: Molecular basis for heterogeneity of the human p53 protein
(C) JOURNAL: Mol. Cell. Biol.
(D) VOLUME: 6
(E) ISSUE: 12
(F) PAGES: 4650-4656
(G) DATE: 1986

(xi) SEQUENCE DESCRIPTION: SEQ ID NO:12:

| | | | | | |
|---|---|---|---|---|---|
| ACCGTCCAGG | GAGCAGGTAG | CTGCTGGGCT | CCGGGGACAC | TTTGCGTTCG | GGCTGGGAGC | 60 |
| GTGCTTTCCA | CGACGGTGAC | ACGCTTCCCT | GGATTGGCAG | CCAGACTGCC | TTCCGGGTCA | 120 |
| CTGCCATGGA | GGAGCCGCAG | TCAGATCCTA | GCGTCGAGCC | CCCTCTGAGT | CAGGAAACAT | 180 |
| TTTCAGACCT | ATGGAAACTA | CTTCCTGAAA | ACAACGTTCT | GTCCCCCTTG | CCGTCCCAAG | 240 |
| CAATGGATGA | TTTGATGCTG | TCCCCGGACG | ATATTGAACA | ATGGTTCACT | GAAGACCCAG | 300 |
| GTCCAGATGA | AGCTCCCAGA | ATGCCAGAGG | CTGCTCCCCG | CGTGGCCCCT | GCACCAGCGA | 360 |
| CTCCTACACC | GGCGGCCCCT | GCACCAGCCC | CCTCCTGGCC | CCTGTCATCT | TCTGTCCCTT | 420 |
| CCCAGAAAAC | CTACCAGGGC | AGCTACGGTT | TCCGTCTGGG | CTTCTTGCAT | TCTGGGACAG | 480 |
| CCAAGTCTGT | GACTTGCACG | TACTCCCCTG | CCCTCAACAA | GATGTTTTGC | CAACTGGCCA | 540 |
| AGACCTGCCC | TGTGCAGCTG | TGGGTTGATT | CCACACCCCC | GCCCGGCACC | CGCGTCCGCG | 600 |
| CCATGGCCAT | CTACAAGCAG | TCACAGCACA | TGACGGAGGT | TGTGAGGCGC | TGCCCCCACC | 660 |
| ATGAGCGCTG | CTCAGATAGC | GATGGTCTGG | CCCCTCCTCA | GCATCTTATC | CGAGTGGAAG | 720 |
| GAAATTTGCG | TGTGGAGTAT | TTGGATGACA | GAAACACTTT | TCGACATAGT | GTGGTGGTGC | 780 |
| CCTATGAGCC | GCCTGAGGTT | GGCTCTGACT | GTACCACCAT | CCACTACAAC | TACATGTGTA | 840 |
| ACAGTTCCTG | CATGGGCGGC | ATGAACCGGA | GGCCCATCCT | CACCATCATC | ACACTGGAAG | 900 |
| ACTCCAGTGG | TAATCTACTG | GGACGGAACA | GCTTTGAGGT | GCGTGTTTGT | GCCTGTCCTG | 960 |
| GGAGAGACCG | GCGCACAGAG | GAAGAGAATC | TCCGCAAGAA | AGGGGAGCCT | CACCACGAGC | 1020 |
| TGCCCCCAGG | GAGCACTAAG | CGAGCACTGC | CAACAACAC | CAGCTCCTCT | CCCCAGCCAA | 1080 |
| AGAAGAAACC | ACTGGATGGA | GAATATTTCA | CCCTTCAGAT | CCGTGGGCGT | GAGCGCTTCG | 1140 |
| AGATGTTCCG | AGAGCTGAAT | GAGGCCTTGG | AACTCAAGGA | TGCCCAGGCT | GGGAAGGAGC | 1200 |
| CAGGGGGGAG | CAGGGCTCAC | TCCAGCCACC | TGAAGTCCAA | AAAGGGTCAG | TCTACCTCCC | 1260 |
| GCCATAAAAA | ACTCATGTTC | AAGACAGAAG | GGCCTGACTC | AGACTGA | | 1307 |

(2) INFORMATION FOR SEQ ID NO:13:

(i) SEQUENCE CHARACTERISTICS:
(A) LENGTH: 1303 base pairs
(B) TYPE: nucleic acid
(C) STRANDEDNESS: double
(D) TOPOLOGY: linear (ii) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( v i i i ) POSITION IN GENOME:
    ( B ) MAP POSITION: 17p13.1

( x ) PUBLICATION INFORMATION:
    ( A ) AUTHORS: Harris, N.
    ( C ) JOURNAL: Mol. Cell. Biol
    ( D ) VOLUME: 6
    ( E ) ISSUE: 12
    ( F ) PAGES: 4650-4656
    ( G ) DATE: 1986

( x i ) SEQUENCE DESCRIPTION: SEQ ID NO:13:

```
GTCCAGGAGC AGGTAGCTGC TGGGCTCCGG GGACACTTTG CGTTCGGGCT GGGAGCGTGC      60
TTTCCACGAC GGTGACACGC TTCCCTGGAT TGGCAGCCAG ACTGCCTTCC GGGTCACTGC     120
CATGGAGGAG CCGCAGTCAG ATCCTAGCGT CGAGCCCCCT CTGAGTCAGG AAACATTTTC     180
AGACCTATGG AAACTACTTC CTGAAAACAA CGTTCTGTCC CCCTTGCCGT CCCAAGCAAT     240
GGATGATTTG ATGCTGTCCC CGGACGATAT TGAACAATGG TTCACTGAAG ACCCAGGTCC     300
AGATGAAGCT CCCAGAATGC CAGAGGCTGC TCCCCCCGTG GCCCCTGCAC CAGCGACTCC     360
TACACCGGCG GCCCCTGCAC CAGCCCCCTC CTGGCCCCTG TCATCTTCTG TCCCTTCCCA     420
GAAAACCTAC CAGGGCAGCT ACGGTTTCCG TCTGGGCTTC TTGCATTCTG GACAGCCAA     480
GTCTGTGACT TGCACGTACT CCCCTGCCCT CAACAAGATG TTTTGCCAAC TGGCCAAGAC     540
CTGCCCTGTG CAGCTGTGGG TTGATTCCAC ACCCCGCCC GGCACCCGCG TCCGCGCCAT     600
GGCCATCTAC AAGCAGTCAC AGCACATGAC GGAGGTTGTG AGGCGCTGCC CCACCATGA     660
GCGCTGCTCA GATAGCGATG GTCTGGCCCC TCCTCAGCAT CTTATCCGAG TGGAAGGAAA     720
TTTGCGTGTG GAGTATTTGG ATGACAGAAA CACTTTTCGA CATAGTGTGG TGGTGCCCTA     780
TGAGCCGCCT GAGGTTGGCT CTGACTGTAC CACCATCCAC TACAACTACA TGTGTAACAG     840
TTCCTGCATG GGCGGCATGA ACCGGAGGCC CATCCTCACC ATCATCACAC TGGAAGACTC     900
CAGTGGTAAT CTACTGGGAC GGAACAGCTT TGAGGTGCGT GTTTGTGCCT GTCCTGGGAG     960
AGACCGGCGC ACAGAGGAAG AGAATCTCCG CAAGAAAGGG GAGCCTCACC ACGAGCTGCC    1020
CCCAGGGAGC ACTAAGCGAG CACTGCCCAA CAACACCAGC TCCTCTCCCC AGCCAAAGAA    1080
GAAACCACTG GATGGAGAAT ATTTCACCCT TCAGATCCGT GGGCGTGAGC GCTTCGAGAT    1140
GTTCCGAGAG CTGAATGAGG CCTTGGAACT CAAGGATGCC AGGCTGGGA AGGAGCCAGG    1200
GGGGAGCAGG GCTCACTCCA GCCACCTGAA GTCCAAAAAG GGTCAGTCTA CCTCCCGCCA    1260
TAAAAAACTC ATGTTCAAGA CAGAAGGGCC TGACTCAGAC TGA                      1303
```

( 2 ) INFORMATION FOR SEQ ID NO:14:

( i ) SEQUENCE CHARACTERISTICS:
        ( A ) LENGTH: 528 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:

(A) ORGANISM: Homo sapiens (viii) POSITION IN GENOME:
    (A) CHROMOSOME/SEGMENT: exon 1

(x) PUBLICATION INFORMATION:
    (A) AUTHORS: Lamb, P.
                    Crawford, L.
    (B) TITLE: Characterization of the human p53 gene
    (C) JOURNAL: Mol. Cell. Biol.
    (D) VOLUME: 6
    (E) ISSUE: 5
    (F) PAGES: 1379-1385
    (G) DATE: 1986

(xi) SEQUENCE DESCRIPTION: SEQ ID NO:14:

```
GGGAGAAAAC  GTTAGGGTGT  GGATATTACG  GAAAGCCTTC  CTAAAAAATG  ACATTTAACT        60
GATGAGAAGA  AAGGATCCAG  CTGAGAGCAA  ACGCAAAAGC  TTTCTTCCTT  CCACCCTTCT       120
ATTTGACACA  ATGCAGGATT  CCTCCAAAAT  GATTTCCACC  AATTCTGCCC  TCACAGCTCT       180
GGCTTGCAGA  ATTTTCCACC  CCAAAATGTT  AGTATCTACG  GCACCAGGTC  GGCGAGAACC       240
TGACTCTGCA  CCCTCCTCCC  CAACTCCATT  TCCTTTGCTT  CCTCCGGCAG  GCGGATTACT       300
TGCCCTTACT  TGTCATGGCG  ACTGTCCAGC  TTTGTGCCAG  GAGCCTCGCA  GGGGTTGTGG       360
GATTGGGGTT  TTCCCCTCCC  ATGTGCTCAA  GACTGGCGCT  AAAAGTTTTG  AGCTTCTCAA       420
AAGTCTAGAG  CCACCGTCCA  GGGAGCAGGT  AGCTGCTGGG  CTCCGGGGAC  ACTTTGGTTC       480
GGGCTGGGAG  CGTGCTTTCC  ACGACGGTGA  CACGCTTCCC  TGGATTGG                     528
```

(2) INFORMATION FOR SEQ ID NO:15:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: exon 2

(x) PUBLICATION INFORMATION:
        (A) AUTHORS: Lamb,
        (C) JOURNAL: Mol. Cell. Biol.
        (D) VOLUME: 6
        (E) ISSUE: 5
        (F) PAGES: 1379-1385
        (G) DATE: 1986

(xi) SEQUENCE DESCRIPTION: SEQ ID NO:15:

```
CAGCCAGACT  GCCTTCCGGG  TCACTGCCAT  GGAGGAGCCG  CAGTCAGATC  CTAGCGTCGA        60
GCCCCCTCTG  AGTCAGGAAA  CATTTTCAGA  CCTATGGAAA  CT                          102
```

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( v i i i ) POSITION IN GENOME:
    ( A ) CHROMOSOME/SEGMENT: exon 3

( x ) PUBLICATION INFORMATION:
    ( A ) AUTHORS: Lamb,
    ( C ) JOURNAL: Mol. Cell. Biol.
    ( D ) VOLUME: 6
    ( E ) ISSUE: 5
    ( F ) PAGES: 1379-1385
    ( G ) DATE: 1986

( x i ) SEQUENCE DESCRIPTION: SEQ ID NO:16:

```
ACTTCCTGAA AACAACGTTC TG                                              22
```

( 2 ) INFORMATION FOR SEQ ID NO:17:

( i ) SEQUENCE CHARACTERISTICS:
        ( A ) LENGTH: 279 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( A ) CHROMOSOME/SEGMENT: exon 4

( x ) PUBLICATION INFORMATION:
        ( A ) AUTHORS: Lamb,
        ( C ) JOURNAL: Mol. Cell. Biol.
        ( D ) VOLUME: 6
        ( E ) ISSUE: 5
        ( F ) PAGES: 1379-1385
        ( G ) DATE: 1986

( x i ) SEQUENCE DESCRIPTION: SEQ ID NO:17:

```
TCCCCCTTGC CGTCCCAAGC AATGGATGAT TTGATGCTGT CCCCGGACGA TATTGAACAA       60
TGGTTCACTG AAGACCCAGG TCCAGATGAA GCTCCCAGAA TGCCAGAGGC TGCTCCCCGC      120
GTGGCCCCTG GACCAGCAGC TCCTACACCG GCGGCCCCTG CACCAGCCCC CTCCTGGCCC      180
CTGTCATCTT CTGTCCCTTC CCAGAAAACC TACCAGGGCA GCTACGGTTT CCGTCTGGGC      240
TTCTTGCATT CTGGGACAGC CAAGTCTGTG ACTTGCACG                             279
```

( 2 ) INFORMATION FOR SEQ ID NO:18:

( i ) SEQUENCE CHARACTERISTICS:
        ( A ) LENGTH: 184 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:

(A) ORGANISM: Homo sapiens (viii) POSITION IN GENOME:
        (A) CHROMOSOME/SEGMENT: exon 5

(x) PUBLICATION INFORMATION:
        (A) AUTHORS: Lamb,
        (C) JOURNAL: Mol. Cell. Biol.
        (D) VOLUME: 6
        (E) ISSUE: 5
        (F) PAGES: 1379-1385
        (G) DATE: 1986

(xi) SEQUENCE DESCRIPTION: SEQ ID NO:18:

TACTCCCCTG CCCTCAACAA GATGTTTTGC CAACTGGCCA AGACCTGCCC TGTGCAGCTG    60

TGGGTTGATT CCACACCCCC GCCCGGCACC CGCGTCCGCG CCATGGCCAT CTACAAGCAG   120

TCACAGCACA TGACGGAGGT TGTGAGGCGC TGCCCCCACC ATGAGCGCTG CTCAGATAGC   180

GATG                                                                184

(2) INFORMATION FOR SEQ ID NO:19:

(i) SEQUENCE CHARACTERISTICS:
        (A) LENGTH: 113 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: exon 6

(x) PUBLICATION INFORMATION:
        (A) AUTHORS: Lamb,
        (C) JOURNAL: Mol. Cell. Biol.
        (D) VOLUME: 6
        (E) ISSUE: 5
        (F) PAGES: 1379-1385
        (G) DATE: 1986

(xi) SEQUENCE DESCRIPTION: SEQ ID NO:19:

GTCTGGCCCC TCCTCAGCAT CTTATCCGAG TGGAAGGAAA TTTGCGTGTG GAGTATTTGG    60

ATGACAGAAA CACTTTTCGA CATAGTGTGG TGGTGCCCTA TGAGCCGCCT GAG          113

(2) INFORMATION FOR SEQ ID NO:20:

(i) SEQUENCE CHARACTERISTICS:
        (A) LENGTH: 110 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: exon 7

(x) PUBLICATION INFORMATION:

(A) AUTHORS: Lamb,
            (C) JOURNAL: Mol. Cell. Biol.
            (D) VOLUME: 6
            (E) ISSUE: 5
            (F) PAGES: 1379-1385
            (G) DATE: 1986

(xi) SEQUENCE DESCRIPTION: SEQ ID NO:20:

GTTGGCTCTG ACTGTACCAC CATCCACTAC AACTACATGT GTAACAGTTC CTGCATGGGC    60

GGCATGAACC GGAGGCCCAT CCTCACCATC ATCACACTGG AAGACTCCAG              110

(2) INFORMATION FOR SEQ ID NO:21:

(i) SEQUENCE CHARACTERISTICS:
            (A) LENGTH: 137 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens (viii) POSITION IN GENOME:
            (A) CHROMOSOME/SEGMENT: exon 8

(x) PUBLICATION INFORMATION:
            (A) AUTHORS: Lamb,
            (C) JOURNAL: Mol. Cell. Biol.
            (D) VOLUME: 6
            (E) ISSUE: 5
            (F) PAGES: 1379-1385
            (G) DATE: 1986

(xi) SEQUENCE DESCRIPTION: SEQ ID NO:21:

TGGTAATCTA CTGGGACGGA ACAGCTTTGA GGTGCGTGTT TGTGCCTGTC CTGGGAGAGA    60

CCGGCGCACA GAGGAAGAGA ATCTCCGCAA GAAAGGGGAG CCTCACCACG AGCTGCCCCC    120

AGGGAGCACT AAGCGAG                                                  137

(2) INFORMATION FOR SEQ ID NO:22:

(i) SEQUENCE CHARACTERISTICS:
            (A) LENGTH: 74 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens (viii) POSITION IN GENOME:
            (A) CHROMOSOME/SEGMENT: exon 9

(xi) SEQUENCE DESCRIPTION: SEQ ID NO:22:

CACTGCCCAA CAACACCAGC TCCTCTCCCC AGCCAAAGAA GAAACCACTG GATGGAGAAT    60

ATTTCACCCT TCAG                                                     74

(2) INFORMATION FOR SEQ ID NO:23:

(  i  ) SEQUENCE CHARACTERISTICS:
    ( A ) LENGTH: 107 base pairs
    ( B ) TYPE: nucleic acid
    ( C ) STRANDEDNESS: double
    ( D ) TOPOLOGY: linear (  i i  ) MOLECULE TYPE: cDNA (  i i i  ) HYPOTHETICAL: NO (  i v  ) ANTI-SENSE: NO (  v i  ) ORIGINAL SOURCE:
    ( A ) ORGANISM: Homo sapiens (  v i i i  ) POSITION IN GENOME:
    ( A ) CHROMOSOME/SEGMENT: exon 10

(  x  ) PUBLICATION INFORMATION:
    ( A ) AUTHORS: Lamb,
    ( C ) JOURNAL: Mol. Cell. Biol.
    ( D ) VOLUME: 6
    ( E ) ISSUE: 5
    ( F ) PAGES: 1379-1385
    ( G ) DATE: 1986

(  x i  ) SEQUENCE DESCRIPTION: SEQ ID NO:23:

| | | | | | | |
|---|---|---|---|---|---|---|
| ATCCGTGGGC | GTGAGCGCTT | CGAGATGTTC | CGAGAGCTGA | ATGAGGCCTT | GGAACTCAAG | 60 |
| GATGCCCAGG | CTGGGAAGGA | GCCAGGGGGG | AGCAGGGCTC | ACTCCAG | | 107 |

( 2 ) INFORMATION FOR SEQ ID NO:24:

(  i  ) SEQUENCE CHARACTERISTICS:
    ( A ) LENGTH: 1288 base pairs
    ( B ) TYPE: nucleic acid
    ( C ) STRANDEDNESS: double
    ( D ) TOPOLOGY: linear (  i i  ) MOLECULE TYPE: cDNA (  i i i  ) HYPOTHETICAL: NO (  i v  ) ANTI-SENSE: NO (  v i  ) ORIGINAL SOURCE:
    ( A ) ORGANISM: Homo sapiens (  v i i i  ) POSITION IN GENOME:
    ( A ) CHROMOSOME/SEGMENT: exon 11

(  x  ) PUBLICATION INFORMATION:
    ( A ) AUTHORS: Lamb,
    ( C ) JOURNAL: Mol. Cell. Biol.
    ( D ) VOLUME: 6
    ( E ) ISSUE: 5
    ( F ) PAGES: 1379-1385
    ( G ) DATE: 1986

(  x i  ) SEQUENCE DESCRIPTION: SEQ ID NO:24:

| | | | | | | |
|---|---|---|---|---|---|---|
| CCACCTGAAG | TCCAAAAAGG | GTCAGTCTAC | CTCCCGCCAT | AAAAAACTCA | TGTTCAAGAC | 60 |
| AGAAGGGCCT | GACTCAGACT | GACATTCTCC | ACTTCTTGTT | CCCCACTGAC | AGCCTCCCAC | 120 |
| CCCCATCTCT | CCCTCCCCTG | CCATTTGGG | TTTTGGGTCT | TTGAACCCTT | GCTTGCAATA | 180 |
| GGTGTGCGTC | AGAAGCACCC | AGGACTTCCA | TTTGCTTTGT | CCCGGGGCTC | CACTGAACAA | 240 |
| GTTGGCCTGC | ACTGGTGTTT | TGTTGTGGGG | AGGAGGATGG | GGAGTAGGAC | ATACCAGCTT | 300 |
| AGATTTTAAG | GTTTTACTG | TGAGGGATGT | TTGGGAGATG | TAAGAAATGT | TCTTGCAGTT | 360 |
| AAGGGTTAGT | TTACAATCAG | CCACATTCTA | GGTAGGGGCC | CACTTCACCG | TACTAACCAG | 420 |
| GGAAGCTGTC | CCTCACTGTT | GAATTTTCTC | TAACTTCAAG | GCCCATATCT | GTGAAATGCT | 480 |
| GGCATTTGCA | CCTACCTCAC | AGAGTGCATT | GTGAGGGTTA | ATGAAATAAT | GTACATCTGG | 540 |

```
CCTTGAAACC ACCTTTTATT ACATGGGGTC TAGAACTTGA CCCCCTTGAG GGTGCTTGTT    600
CCCTCTCCCT GTTGGTCGGT GGGTTGGTAG TTTCTACAGT TGGGCAGCTG GTTAGGTAGA    660
GGGAGTTGTC AAGTCTCTGC TGGCCCAGCC AAACCCTGTC TGACAACCTC TTGGTGAACC    720
TTAGTACCTA AAAGGAAATC TCACCCCATC CCACACCCTG GAGGATTTCA TCTCTTGTAT    780
ATGATGATCT GGATCCACCA AGACTTGTTT TATGCTCAGG GTCAATTTCT TTTTCTTTT     840
TTTTTTTTTT TTTCTTTTTC TTTGAGACTG GGTCTCGCTT TGTTGCCCAG GCTGGAGTGG    900
AGTGGCGTGA TCTTGGCTTA CTGCAGCCTT TGCCTCCCCG GCTCGAGCAG TCCTGCCTCA    960
GCCTCCGGAG TAGCTGGGAC CACAGGTTCA TGCCACCATG GCCAGCCAAC TTTTGCATGT   1020
TTTGTAGAGA TGGGGTCTCA CAGTGTTGCC CAGGCTGGTC TCAAACTCCT GGGCTCAGGC   1080
GATCCACCTG TCTCAGCCTC CCAGAGTGCT GGGATTACAA TTGTGAGCCA CCACGTCCAG   1140
CTGGAAGGGT CAACATCTTT TACATTCTGC AAGCACATCT GCATTTCAC CCCACCCTTC    1200
CCCTCCTTCT CCCTTTTTAT ATCCATTTT TATATCGATC TCTTATTTTA CAATAAAACT    1260
TTGCTGCCAC CTGTGTGTCT GAGGGGTG                                     1288
```

( 2 ) INFORMATION FOR SEQ ID NO:25:

( i ) SEQUENCE CHARACTERISTICS:
        ( A ) LENGTH: 393 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Homo sapiens ( x ) PUBLICATION INFORMATION:
        ( A ) AUTHORS: Buchman, et al.,
        ( C ) JOURNAL: Gene
        ( D ) VOLUME: 70
        ( F ) PAGES: 245-252
        ( G ) DATE: 1988

( x i ) SEQUENCE DESCRIPTION: SEQ ID NO:25:

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140
```

| | | | | | | | | | | | | | | |
|---|---|---|---|---|---|---|---|---|---|---|---|---|---|---|
| Leu | Trp | Val | Asp | Ser | Thr | Pro | Pro | Pro | Gly | Thr | Arg | Val | Arg | Ala | Met |
| 145 | | | | | 150 | | | | | 155 | | | | | 160 |
| Ala | Ile | Tyr | Lys | Gln | Ser | Gln | His | Met | Thr | Glu | Val | Val | Arg | Arg | Cys |
| | | | | 165 | | | | | 170 | | | | | 175 | |
| Pro | His | His | Glu | Arg | Cys | Ser | Asp | Ser | Asp | Gly | Leu | Ala | Pro | Pro | Gln |
| | | | 180 | | | | | 185 | | | | | 190 | | |
| His | Leu | Ile | Arg | Val | Glu | Gly | Asn | Leu | Arg | Val | Glu | Tyr | Leu | Asp | Asp |
| | | 195 | | | | | 200 | | | | | 205 | | | |
| Arg | Asn | Thr | Phe | Arg | His | Ser | Val | Val | Val | Pro | Tyr | Glu | Pro | Pro | Glu |
| | 210 | | | | | 215 | | | | | 220 | | | | |
| Val | Gly | Ser | Asp | Cys | Thr | Thr | Ile | His | Tyr | Asn | Tyr | Met | Cys | Asn | Ser |
| 225 | | | | | 230 | | | | | 235 | | | | | 240 |
| Ser | Cys | Met | Gly | Gly | Met | Asn | Arg | Arg | Pro | Ile | Leu | Thr | Ile | Ile | Thr |
| | | | | 245 | | | | | 250 | | | | | 255 | |
| Leu | Glu | Asp | Ser | Ser | Gly | Asn | Leu | Leu | Gly | Arg | Asn | Ser | Phe | Glu | Val |
| | | | 260 | | | | | 265 | | | | | 270 | | |
| Arg | Val | Cys | Ala | Cys | Pro | Gly | Arg | Asp | Arg | Arg | Thr | Glu | Glu | Glu | Asn |
| | | 275 | | | | | 280 | | | | | 285 | | | |
| Leu | Arg | Lys | Lys | Gly | Glu | Pro | His | His | Glu | Leu | Pro | Pro | Gly | Ser | Thr |
| | 290 | | | | | 295 | | | | | 300 | | | | |
| Lys | Arg | Ala | Leu | Pro | Asn | Asn | Thr | Ser | Ser | Ser | Pro | Gln | Pro | Lys | Lys |
| 305 | | | | | 310 | | | | | 315 | | | | | 320 |
| Lys | Pro | Leu | Asp | Gly | Glu | Tyr | Phe | Thr | Leu | Gln | Ile | Arg | Gly | Arg | Glu |
| | | | | 325 | | | | | 330 | | | | | 335 | |
| Arg | Phe | Glu | Met | Phe | Arg | Glu | Leu | Asn | Glu | Ala | Leu | Glu | Leu | Lys | Asp |
| | | | 340 | | | | | 345 | | | | | 350 | | |
| Ala | Gln | Ala | Gly | Lys | Glu | Pro | Gly | Gly | Ser | Arg | Ala | His | Ser | Ser | His |
| | | | 355 | | | | | 360 | | | | | 365 | | |
| Leu | Lys | Ser | Lys | Lys | Gly | Gln | Ser | Thr | Ser | Arg | His | Lys | Lys | Leu | Met |
| | 370 | | | | | 375 | | | | | 380 | | | | |
| Phe | Lys | Thr | Glu | Gly | Pro | Asp | Ser | Asp |
| 385 | | | | | 390 | | | |

(2) INFORMATION FOR SEQ ID NO:26:

(i) SEQUENCE CHARACTERISTICS:
        (A) LENGTH: 393 amino acids
        (B) TYPE: amino acid
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Homo sapiens (x) PUBLICATION INFORMATION:
        (A) AUTHORS: Harris, et al.,
        (C) JOURNAL: Mol. Cell. Biol.
        (D) VOLUME: 6
        (E) ISSUE: 12
        (F) PAGES: 4650-4656
        (G) DATE: 1986

(xi) SEQUENCE DESCRIPTION: SEQ ID NO:26:

| | | | | | | | | | | | | | | |
|---|---|---|---|---|---|---|---|---|---|---|---|---|---|---|
| Met | Glu | Glu | Pro | Gln | Ser | Asp | Pro | Ser | Val | Glu | Pro | Pro | Leu | Ser | Gln |
| 1 | | | | 5 | | | | | 10 | | | | | 15 | |
| Glu | Thr | Phe | Ser | Asp | Leu | Trp | Lys | Leu | Leu | Pro | Glu | Asn | Asn | Val | Leu |
| | | | 20 | | | | | 25 | | | | | 30 | | |

Ser Pro Leu Pro Ser Gln Ala Met Asp Asp Leu Met Leu Ser Pro Asp
 35                  40                  45

Asp Ile Glu Gln Trp Phe Thr Glu Asp Pro Gly Pro Asp Glu Ala Pro
 50                  55                  60

Arg Met Pro Glu Ala Ala Pro Arg Val Ala Pro Ala Pro Ala Thr Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

( 2 ) INFORMATION FOR SEQ ID NO:27:

( i ) SEQUENCE CHARACTERISTICS:
        ( A ) LENGTH: 393 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
    ( A ) ORGANISM: Homo sapiens ( x ) PUBLICATION INFORMATION:
    ( A ) AUTHORS: Harris, et al.,
    ( C ) JOURNAL: Mol. Cell. Biol.
    ( D ) VOLUME: 6
    ( E ) ISSUE: 12
    ( F ) PAGES: 4650-4656
    ( G ) DATE: 1986

( x i ) SEQUENCE DESCRIPTION: SEQ ID NO:27:

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Thr Pro
65                      70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335
```

```
        Arg  Phe  Glu  Met  Phe  Arg  Glu  Leu  Asn  Glu  Ala  Leu  Glu  Leu  Lys  Asp
                       340                      345                     350

Ala  Gln  Ala  Gly  Lys  Glu  Pro  Gly  Gly  Ser  Arg  Ala  His  Ser  Ser  His
                       355                      360                     365

Leu  Lys  Ser  Lys  Lys  Gly  Gln  Ser  Thr  Ser  Arg  His  Lys  Lys  Leu  Met
                       370                      375                     380

Phe  Lys  Thr  Glu  Gly  Pro  Asp  Ser  Asp
                       385                      390
```

( 2 ) INFORMATION FOR SEQ ID NO:28:

( i ) SEQUENCE CHARACTERISTICS:
        ( A ) LENGTH: 393 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Homo sapiens ( x ) PUBLICATION INFORMATION:
        ( A ) AUTHORS: Lamb, P.
                      Crawford, L.
        ( C ) JOURNAL: Mol. Cell. Biol.
        ( D ) VOLUME: 6
        ( E ) ISSUE: 5
        ( F ) PAGES: 1379-1385
        ( G ) DATE: 1986

( x i ) SEQUENCE DESCRIPTION: SEQ ID NO:28:

```
        Met  Glu  Glu  Pro  Gln  Ser  Asp  Pro  Ser  Val  Glu  Pro  Pro  Leu  Ser  Gln
         1                 5                      10                      15

Glu  Thr  Phe  Ser  Asp  Leu  Trp  Lys  Leu  Leu  Pro  Glu  Asn  Asn  Val  Leu
                       20                       25                      30

Ser  Pro  Leu  Pro  Ser  Gln  Ala  Met  Asp  Asp  Leu  Met  Leu  Ser  Pro  Asp
                       35                       40                      45

Asp  Ile  Glu  Gln  Trp  Phe  Thr  Glu  Asp  Pro  Gly  Pro  Asp  Glu  Ala  Pro
                  50                            55                      60

Arg  Met  Pro  Glu  Ala  Ala  Pro  Arg  Val  Ala  Pro  Gly  Pro  Ala  Ala  Pro
        65                      70                       75                          80

Thr  Pro  Ala  Ala  Pro  Ala  Pro  Ala  Pro  Ser  Trp  Pro  Leu  Ser  Ser  Ser
                            85                       90                           95

Val  Pro  Ser  Gln  Lys  Thr  Tyr  Gln  Gly  Ser  Tyr  Gly  Phe  Arg  Leu  Gly
                       100                      105                     110

Phe  Leu  His  Ser  Gly  Thr  Ala  Lys  Ser  Val  Thr  Cys  Thr  Tyr  Ser  Pro
                       115                      120                     125

Ala  Leu  Asn  Lys  Met  Phe  Cys  Gln  Leu  Ala  Lys  Thr  Cys  Pro  Val  Gln
                       130                      135                     140

Leu  Trp  Val  Asp  Ser  Thr  Pro  Pro  Pro  Gly  Thr  Arg  Val  Arg  Ala  Met
        145                     150                      155                         160

Ala  Ile  Tyr  Lys  Gln  Ser  Gln  His  Met  Thr  Glu  Val  Val  Arg  Arg  Cys
                       165                      170                     175

Pro  His  His  Glu  Arg  Cys  Ser  Asp  Ser  Asp  Gly  Leu  Ala  Pro  Pro  Gln
                       180                      185                     190

His  Leu  Ile  Arg  Val  Glu  Gly  Asn  Leu  Arg  Val  Glu  Tyr  Leu  Asp  Asp
                       195                      200                     205
```

| | | | | | | | | | | | | | | |
|---|---|---|---|---|---|---|---|---|---|---|---|---|---|---|
| Arg | Asn 210 | Thr | Phe | Arg | His | Ser 215 | Val | Val | Val | Pro | Tyr 220 | Glu | Pro | Pro | Glu |
| Val 225 | Gly | Ser | Asp | Cys | Thr 230 | Thr | Ile | His | Tyr | Asn 235 | Tyr | Met | Cys | Asn | Ser 240 |
| Ser | Cys | Met | Gly | Gly 245 | Met | Asn | Arg | Arg | Pro 250 | Ile | Leu | Thr | Ile | Ile 255 | Thr |
| Leu | Glu | Asp | Ser 260 | Ser | Gly | Asn | Leu | Leu 265 | Gly | Arg | Asn | Ser | Phe 270 | Glu | Val |
| Arg | Val | Cys 275 | Ala | Cys | Pro | Gly | Arg 280 | Asp | Arg | Arg | Thr | Glu 285 | Glu | Glu | Asn |
| Leu | Arg 290 | Lys | Lys | Gly | Glu | Pro 295 | His | His | Glu | Leu | Pro 300 | Pro | Gly | Ser | Thr |
| Lys 305 | Arg | Ala | Leu | Pro | Asn 310 | Asn | Thr | Ser | Ser | Ser 315 | Pro | Gln | Pro | Lys | Lys 320 |
| Lys | Pro | Leu | Asp | Gly 325 | Glu | Tyr | Phe | Thr | Leu 330 | Gln | Ile | Arg | Gly | Arg 335 | Glu |
| Arg | Phe | Glu | Met 340 | Phe | Arg | Glu | Leu | Asn 345 | Glu | Ala | Leu | Glu | Leu 350 | Lys | Asp |
| Ala | Gln | Ala 355 | Gly | Lys | Glu | Pro | Gly 360 | Gly | Ser | Arg | Ala | His 365 | Ser | Ser | His |
| Leu | Lys 370 | Ser | Lys | Lys | Gly | Gln 375 | Ser | Thr | Ser | Arg | His 380 | Lys | Lys | Leu | Met |
| Phe 385 | Lys | Thr | Glu | Gly | Pro 390 | Asp | Ser | Asp | | | | | | | |